United States Patent
Smith et al.

(10) Patent No.: US 11,877,742 B2
(45) Date of Patent: *Jan. 23, 2024

(54) ADJUSTABLE COMPRESSION STAPLE AND METHOD FOR STAPLING WITH ADJUSTABLE COMPRESSION

(71) Applicant: Cilag GmbH International, Zug (CH)

(72) Inventors: Kevin W. Smith, Coral Gables, FL (US); Matthew A. Palmer, Miami, FL (US); Korey Kline, Miami, FL (US); Derek Dee Deville, Coral Gables, FL (US)

(73) Assignee: Cilag GmbH International, Zug (CH)

( * ) Notice: Subject to any disclaimer, the term of this patent is extended or adjusted under 35 U.S.C. 154(b) by 994 days.

This patent is subject to a terminal disclaimer.

(21) Appl. No.: 16/738,771

(22) Filed: Jan. 9, 2020

(65) Prior Publication Data

US 2020/0146675 A1    May 14, 2020

Related U.S. Application Data

(62) Division of application No. 15/614,666, filed on Jun. 6, 2017, now Pat. No. 10,568,620, which is a division
(Continued)

(51) Int. Cl.
*A61B 17/064* (2006.01)
*F16B 15/00* (2006.01)

(52) U.S. Cl.
CPC ........ *A61B 17/0644* (2013.01); *A61B 17/064* (2013.01); *F16B 15/0015* (2013.01)

(58) Field of Classification Search
CPC .......... A61B 17/00644; A61B 17/0064; A61B 2017/0065; F16B 15/0015
See application file for complete search history.

(56) References Cited

U.S. PATENT DOCUMENTS

| | | |
|---|---|---|
| 4,278,091 A | 7/1981 | Borzone |
| 4,532,927 A | 8/1985 | Miksza, Jr. |

(Continued)

FOREIGN PATENT DOCUMENTS

| | | |
|---|---|---|
| EP | 0852128 B1 | 7/2001 |
| EP | 1179994 B1 | 12/2006 |

(Continued)

OTHER PUBLICATIONS

Extended European Search Report for European Application No. 16 18 5670 dated Dec. 9, 2016.
(Continued)

*Primary Examiner* — Diane D Yabut
*Assistant Examiner* — Christina C Lauer
(74) *Attorney, Agent, or Firm* — Gregory L. Mayback; Mayback IP Law, P.A.

(57) ABSTRACT

A compression-self-adjusting staple that comprises a substantially U-shaped staple having a bridge, two legs extending from the bridge at an angle thereto, and a compression device. The compression device is at least partly disposed between the legs and has a bias portion with a compression surface that is movably disposed between the legs and a compression resistor. The compression resistor is connected to the bridge and to the compression surface and is formed into a plurality of bends that resist movement of the compression surface towards the bridge with a pre-set compressive force.

20 Claims, 19 Drawing Sheets

Related U.S. Application Data of application No. 14/164,748, filed on Jan. 27, 2014, now Pat. No. 9,700,306, which is a division of application No. 13/222,758, filed on Aug. 31, 2011, now Pat. No. 8,679,156, which is a division of application No. 11/971,998, filed on Jan. 10, 2008, now Pat. No. 8,679,154, said application No. 14/164,748 is a division of application No. 11/971,998, filed on Jan. 10, 2008, now Pat. No. 8,679,154.

(60) Provisional application No. 60/880,146, filed on Jan. 12, 2007.

(56) References Cited

U.S. PATENT DOCUMENTS

| | | | |
|---|---|---|---|
| 4,887,601 A | 12/1989 | Richards | |
| 5,222,961 A | 6/1993 | Nakao et al. | |
| 5,356,064 A | 10/1994 | Green et al. | |
| 5,393,184 A * | 2/1995 | Beeuwkes, III | H02G 3/26 411/480 |
| 5,484,451 A | 1/1996 | Akopov et al. | |
| 5,540,375 A | 7/1996 | Bolanos et al. | |
| 5,628,446 A | 5/1997 | Geiste et al. | |
| 5,715,987 A | 2/1998 | Kelley et al. | |
| 6,015,417 A | 1/2000 | Reynolds, Jr. | |
| 6,171,320 B1 | 1/2001 | Monassevitch | |
| 6,261,303 B1 | 7/2001 | Mayenberger et al. | |
| 6,402,765 B1 | 6/2002 | Monassevitch et al. | |
| 6,443,973 B1 | 9/2002 | Whitman | |
| 6,802,848 B2 | 10/2004 | Anderson | |
| 6,896,684 B2 | 6/2005 | Monassevitch et al. | |
| 6,981,941 B2 | 1/2006 | Whitman et al. | |
| 7,108,709 B2 | 9/2006 | Cummins | |
| 7,464,847 B2 | 12/2008 | Viola et al. | |
| 7,784,663 B2 | 8/2010 | Shelton, IV | |
| 7,794,475 B2 | 9/2010 | Hess et al. | |
| 8,679,154 B2 * | 3/2014 | Smith | F16B 15/0015 227/175.1 |
| 8,679,156 B2 * | 3/2014 | Smith | A61B 17/064 227/175.1 |
| 9,700,306 B2 * | 7/2017 | Smith | F16B 15/0015 |
| 10,568,620 B2 * | 2/2020 | Smith | A61B 17/064 |
| 2003/0069603 A1 | 4/2003 | Little et al. | |
| 2005/0143759 A1 | 6/2005 | Kelly | |
| 2005/0216056 A1 | 9/2005 | Valdevit et al. | |
| 2005/0256452 A1 | 11/2005 | DeMarchi et al. | |
| 2006/0100646 A1 | 5/2006 | Hart et al. | |
| 2006/0155288 A1 | 7/2006 | Little et al. | |
| 2006/0167480 A1 | 7/2006 | Loshakove et al. | |
| 2006/0282084 A1 * | 12/2006 | Blier | A61B 17/0643 606/329 |
| 2006/0291981 A1 * | 12/2006 | Viola | A61B 17/0644 411/457 |
| 2007/0010854 A1 | 1/2007 | Cummins | |
| 2007/0213747 A1 * | 9/2007 | Monassevitch | A61B 17/122 606/151 |

FOREIGN PATENT DOCUMENTS

| | | |
|---|---|---|
| EP | 1728473 A1 | 12/2006 |
| JP | 1967001089 B2 | 1/1967 |
| JP | 2006-334414 A | 12/2006 |
| JP | 2006334412 | 12/2006 |
| JP | 2014064924 | 4/2014 |

OTHER PUBLICATIONS

Extended European Search Report for European Application No. 08 72 7577 dated Jan. 28, 2011.
International Search Report for International Application No. PCT/US08/50829 dated Aug. 1, 2008.
Notice of Rejection from the Japanese Patent Office for Application No. 2009-545698 dated Oct. 4, 2011.
Notice of Rejection from the Japanese Patent Office for Application No. 2017-113125 dated Apr. 24, 2018.
Notice of Rejection from the Japanese Patent Office for Application No. 2015-192457 dated Aug. 30, 2016.
Notice on the First Office Action and Search Report from the State Intellectual Property Office of The People's Republic of China for Chinese Patent Application No. 201510248868.8 dated Sep. 19, 2016.
Official Communication in European App. 08 727 577.2, dated Jan. 23, 2013.
European Search Report of European App. 13 191 390.7, dated Feb. 25, 2014.
Uropean Search Report of European App. 18 165 766.9, dated Sep. 6, 2018.
Examination Report of Australia App. 2008206439, dated Oct. 29, 2010.
Examination Report of Australia App. 2011218702, dated Jun. 7, 2012.
Examination Report of Australia App. 2013224717, dated Jan. 9, 2015.
Examination Report of Canada App. 2674586, dated Dec. 20, 2011.
Examination Report of Canada App. 2674586, dated Oct. 16, 2012.
Examination Report of Canada App. 2674586, dated May 22, 2014.
Office Action in China App. 200880001983.3, dated Nov. 30, 2010.
Office Action in China App. 200880001983.3, dated Mar. 23, 2012.
Office Action in China App. 200880001983.3, dated Aug. 2, 2012.
Notice on Reexamination of China App. 200880001983.3, dated Mar. 31, 2014.
Office Action in China App. 201510248868.8, dated Jun. 19, 2017.
Office Action in China App. 201510248868.8, dated Apr. 3, 2018.
Examination Report of India App. 4487/DELNP/2009, dated Oct. 6, 2017.
Notice of Rejection of Japan App. 2009-545698, dated Mar. 12, 2013.
Notice of Rejection of Japan App. 2013-212687, dated Dec. 22, 2014.
Notice of Rejection of Japan App. 2017-113125, dated Sep. 14, 2018.
Notice of Rejection of Japan App. 2019-000255, dated Nov. 14, 2019.
Office Action in U.S. Appl. No. 17/645,646, dated Jul. 3, 2023.
Office Action in U.S. Appl. No. 15/447,678, dated Apr. 13, 2023.

* cited by examiner

ADJUSTABLE COMPRESSION STAPLE AND METHOD FOR STAPLING WITH ADJUSTABLE COMPRESSION

CROSS-REFERENCE TO RELATED APPLICATIONS

The present application:
is a divisional of U.S. patent application Ser. No. 15/614,666, filed on Jun. 6, 2017, which:
  is a divisional of U.S. patent application Ser. No. 14/164,748, filed on Jan. 27, 2014, now U.S. Pat. No. 9,700,306, issued on Jul. 11, 2017, which:
    is a divisional of U.S. patent application Ser. No. 13/222,758, filed on Aug. 31, 2011, now U.S. Pat. No. 8,679,156, issued on Mar. 25, 2014, which:
      is a divisional of U.S. patent application Ser. No. 11/971,998, filed on Jan. 10, 2008, now U.S. Pat. No. 8,679,154, issued on Mar. 25, 2014, which:
        claims the benefit, under 35 U.S.C. § 119, of U.S. Provisional Patent Application No. 60/880,146, filed on Jan. 12, 2007; and
  is a divisional of U.S. patent application Ser. No. 11/971,998, filed on Jan. 10, 2008, now U.S. Pat. No. 8,679,154, issued on Mar. 25, 2014, which:
    claims the benefit, under 35 U.S.C. § 119, of U.S. Provisional Patent Application No. 60/880,146, filed on Jan. 12, 2007,
the complete disclosures of which are hereby incorporated by reference herein in their entireties.

STATEMENT REGARDING FEDERALLY SPONSORED RESEARCH OR DEVELOPMENT n/a

FIELD OF THE INVENTION

The present invention lies in the field of staple fastening, in particular, staples and instruments capable of applying a single or a plurality of staples to a material and processes therefor. More particularly, the present invention relates to a staple capable of placing a load-bearing force against the material being stapled and improvements in processes for stapling material. The device can be used, particularly, in the medical field for stapling tissue during surgical procedures, whether open, endoscopic, or laparoscopic.

BACKGROUND OF THE INVENTION

Conventional staples are, typically, U-shaped and require a staple cartridge and anvil to fasten the staple onto a material. The U-shape of the staple can be considered relatively square-cornered because of the sharp angle at which the legs extend from the bridge. On activation of a stapling device, the staple legs are advanced forward so that they penetrate a material on both sides of a slit or opening. As a staple former is advanced further, the legs of the staple bend around the anvil causing the tips of the legs to advance along an arcuate path toward each other so that the staple ultimately assumes a generally rectangular shape, thereby compressing the material that has been trapped between the staple legs, which is tissue in surgical applications. This compression of the material is the mechanism by which a closure is effected. Depending on the length of the incision or opening, a series of staples will be delivered along its length, which can ensure a blood tight closure in surgical procedures.

Because the staple has two legs that pierce the material, they are well suited for fastening two or more layers of material together when used with the opposing anvil. Whether used in an office or during a surgical procedure, most staples 1 have similar shapes—a bridge 2 connecting two relatively parallel legs 4, which legs are disposed approximately orthogonal to the bridge 2, which, depending on the material of the staple, results in a square-cornered U-shape. In surgical stapling devices, it is beneficial to start the legs 4 in a slight outward orientation to assist retention of the staples within the cartridge. The staple illustrated in FIG. 1 is representative of conventional surgical staples. Such staples are compressed against an anvil to bend the tips of the legs 4 inward. For purposes sufficient in surgery, the final stapled configuration has a stapling range from a "least" acceptable orientation to a "greatest" acceptable orientation. The "least" acceptable staple range is a position where the tangent defined by the tip of each leg 4 is at a negative angle to a line parallel to the bridge 2 and touching the lower portions of both legs 4. The "greatest" acceptable staple range is a position where the legs 4 are bent into a shape similar to the letter "B."

The staple 1 of FIG. 1 is shown in an orientation where the tips of the legs 4 are bent slightly by an anvil on the way towards a final stapled form. (This slightly bent orientation is also present with respect to the staples illustrated hereafter.) The legs 4 of such slightly bent staples have three different portions:
  a connecting portion 6 (at which the legs 4 are connected to the bridge 2);
  an intermediate portion 8 (at which the staple is bent; of course it is also possible for the connection portion 6 to be bent for various fastening purposes); and
  a piercing portion 10 (for projecting through the material to be fastened; this portion, too, is bent when fastening).

Many stapling devices exist to deploy such staples. Some surgical stapling instruments are described in U.S. Pat. No. 5,465,895 to Knodel et al., and U.S. Pat. Nos. 6,644,532 and 6,250,532 to Green et al. When the staple 1 is bent for fastening, the polygon formed by the interior sides of the bent staple 1 defines an envelope or a central region 14. The material to be fastened by the staple 1 resides in and is compressed within the central region 14 when stapling occurs. When the final staple orientation is B-shaped, there can be two regions in which the tissue is held and compressed.

One common feature associated with conventional staples is that there is no controllable way of adjusting the compressive force that is applied by the staple to the material being stapled. While items such as paper and cardboard can withstand a wide range of stapler compressive force without breaking or puncturing, living tissue, such as the tissue to be fastened in a surgical procedure, has a limited range of compressive force and cannot withstand force greater than a upper limit within that range without causing tissue damage. In fact, the range of optimal stapling force for a given surgical stapling procedure is relatively small and varies substantially with the type of tissue being stapled.

While it may be true that the distance between the bending point of the legs and the bridge (see, e.g., span 12 in FIG. 1) can be increased to impart less force on material within the staple, this characteristic does not apply when living tissue having varying degrees of hardness, composition, and flexibility is the material being stapled. Even if the staple leg bending distance 12 is increased, if more or less or harder or softer tissue than expected is actually captured within the staple, the force applied to the captured tissue will not be controlled and will not be optimal for that tissue.

When one, two, or more layers of tissue are being stapled, it is desirable for the tissue to be at a desired compressive state so that a desirous medical change can occur, but not to be at an undesired compressive state sufficient to cause tissue necrosis. Because there is no way to precisely control the tissue that is being placed within the staple, it is not possible to ensure that the tissue is stapled within an optimal tissue compression range, referred to as an OTC range. Therefore, ruling out of tissue necrosis is difficult or not possible. Further, tissue presented within one staple may not be the same tissue that is presented within an adjacent staple or is within another staple that is fired during the same stapling procedure. Thus, while one or a few of a set of staples could actually fasten within the OTC range, it is quite possible for many other staples in the same stapling procedure to fasten outside the OTC range.

What is needed, therefore, is an improved staple and improved methods of stapling that allow automatic control of the staple compression force imparted upon the material being stapled so that compression of the material remains within a desired OTC range. While prior art surgical stapling instruments have utility, and may be successfully employed in many medical procedures, it is desirable to enhance their operation with the ability to deliver a staple that can automatically tailor the compression force delivered to the tissue without external mechanics or operations.

BRIEF SUMMARY OF THE INVENTION

It is accordingly an object of the invention to provide an adjustable compression staple and methods for stapling with adjustable compression that overcome the hereinafore-mentioned disadvantages of the heretofore-known devices and methods of this general type and that automatically tailors the compression force delivered to the tissue.

When tissue is stapled, liquid is forced out of the tissue. The OTC range of the tissue is a compression range in which liquid is removed from the tissue (i.e., desiccates the tissue) without damaging or necrosing the tissue. As the liquid from the tissue exits the tissue due to compression exerted upon the tissue by the staple, however, the compressive force that is being imposed upon the tissue naturally reduces—because less mass is between the opposing staple portions. In some instances, this reduction can allow the imparted tissue compression to exit the OTC range. Staples according to the present invention each have a self-adjusting, pre-tensioned compression device that keeps compression force on the interposed tissue within the OTC compression range even after being desiccated.

The prior art staple of FIG. 1 has a stapling range that is illustrated in FIG. 17. For purposes sufficient in surgery, the final stapled configuration of the OTC staples of the present invention has a stapling range that is illustrated, for example, in FIGS. 18 to 20. A "least" acceptable staple range is a position where the tangent T defined by the tip of each leg 4 is at a negative angle α to a line L parallel to the bridge 2. This orientation is illustrated with the left half of the staple in FIG. 17 merely for reasons of clarity. See also FIGS. 18 to 20. A "greatest" acceptable staple range is a position where the legs 4 are bent 180 degrees into a shape similar to the letter "B" (see the exemplary orientation illustrated in the right-half of FIG. 17) but, in comparison to the prior art staple range of FIG. 17, as described below in detail, the tips of the legs 4 of the staples according to the invention reach only up to a compressing portion and not further than this compressing portion as shown in FIG. 20, for example. In such an orientation, the stapled tips of the legs do not interfere with the OTC device present in the staples according to the invention.

The OTC devices for staples according to the invention take many forms. The OTC device can be integral with the legs of the staple and project into a central area or can be attached to the staple to project into the central area. The OTC device can be sinusoidal in shape with a compressing portion at the end of the OTC device or can be have multiple cycles of bends between the bridge of the staple with the compressing portion at the end of the OTC device. The bending portion can be single or double, the double bends being in cycle, out of cycle, mirror-symmetrical, to name a few. The bends can be double-sinusoidal as shown in FIGS. 8, 9, and 11 The OTC device can be contained entirely between the two legs of the staple or can encircle one or both of the legs and, thereby, use the legs as a guide, for example, a sliding guide. The leg encirclement by the OTC device can be single or multiple. Travel of the OTC device can be limited, for example, by a star washer. The OTC device can be a compression spring(s) and a plate(s), with the plate encircling the legs and sliding thereon. The OTC device can be a compressible material secured on the legs. This material can be in the shape of a plate or a pillow.

With the foregoing and other objects in view, there is provided, in accordance with the invention, a substantially U-shaped staple having a bridge, legs, and an internally disposed compression device having a bias portion with a compression surface movably disposed between the legs and a compression resistor connected to the bridge and to the compression surface and is formed to resist movement of the compression surface towards the bridge with a force.

In accordance with another feature of the invention, the bridge is substantially rod-shaped with ends and the base end of each of the legs is integral with a respective one of the ends.

In accordance with a further feature of the invention, the bridge and legs define a bridge-leg plane and the legs extend from the bridge at an angle of between 80 and 100 degrees in the bridge-leg plane.

In accordance with an additional feature of the invention, the compression surface defines two orifices and each of the legs extends through one of the two orifices.

In accordance with yet another feature of the invention, the compression resistor defines at least one orifice pair, the compression surface defines two orifices, and each of the legs extends through one of the two orifices and one of the at least one orifice pair.

In accordance with yet a further feature of the invention, the compression resistor defines a plurality of orifice pairs, the compression surface defines two orifices, and each of the legs extends through one of the two orifices and one of each of the orifice pairs.

In accordance with yet an added feature of the invention, the bridge and the legs define a compression axis and the compression surface is movably disposed between the legs along the compression axis.

In accordance with yet an additional feature of the invention, the compression device is connected to the bridge.

In accordance with again another feature of the invention, the compression resistor connects the bridge to the compression surface.

In accordance with again a further feature of the invention, the bridge, the legs, the compression resistor, and the compression surface are integral.

In accordance with again an added feature of the invention, the compression resistor is at least partly disposed between the legs.

In accordance with again an additional feature of the invention, the compression resistor is disposed between the bridge and the compression surface.

In accordance with still another feature of the invention, the force is a pre-defined opposing force.

In accordance with still a further feature of the invention, the force is a substantially constant force.

In accordance with still an added feature of the invention, the force is a linearly increasing force.

In accordance with still an additional feature of the invention, the compression resistor has an anti-compressive spring constant imparting a substantially constant anti-compressive force over a pre-defined compression range.

In accordance with another feature of the invention, the staple and the compression device are of a biocompatible material.

In accordance with a further feature of the invention, the compression surface and the legs define a central compression region in which is to be disposed a material to be compressed between the compression surface and stapling points when distal ends of the staple legs are deformed. When the distal ends are deformed in a staple closing direction into the central compression region, the bias portion resists movement of the compression surface in the staple closing direction with a pre-defined, substantially constant force.

In accordance with an added feature of the invention, the compression surface and the bias portion are shaped to impart a pre-defined, substantially constant bias force upon material disposed between the compression surface and stapling points when the stapling points are deformed.

In accordance with a concomitant feature of the invention, when stapling points are deformed toward one another, material disposed between the compression surface and the stapling points is compressed between the stapling points and the compression surface. The compression resistor maintains a substantially constant compressive force on the material within a pre-defined range independent of a degree of compression between stapling points and the compression surface.

Although the invention is illustrated and described herein as embodied in an adjustable compression staple and method for stapling with adjustable compression, it is, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

Other features that are considered as characteristic for the invention are set forth in the appended claims. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures. The figures of the drawings are not drawn to scale.

Before the present invention is disclosed and described, it is to be understood that the terminology used herein is for the purpose of describing particular embodiments only and is not intended to be limiting. The terms "a" or "an", as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically.

As used herein, the term "about" or "approximately" applies to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure.

BRIEF DESCRIPTION OF THE DRAWINGS

Advantages of the embodiments of the present invention will be apparent from the following detailed description of the preferred embodiments thereof, which description should be considered in conjunction with the accompanying drawings in which.

DETAILED DESCRIPTION OF THE PREFERRED EMBODIMENTS

Herein various embodiment of the present invention are described. In many of the different embodiments, features are similar. Therefore, to avoid redundancy, repetitive description of these similar features may not be made in some circumstances. It shall be understood, however, that description of a first-appearing feature applies to the later described similar feature and each respective description, therefore, is to be incorporated therein without such repetition.

Figure 1:
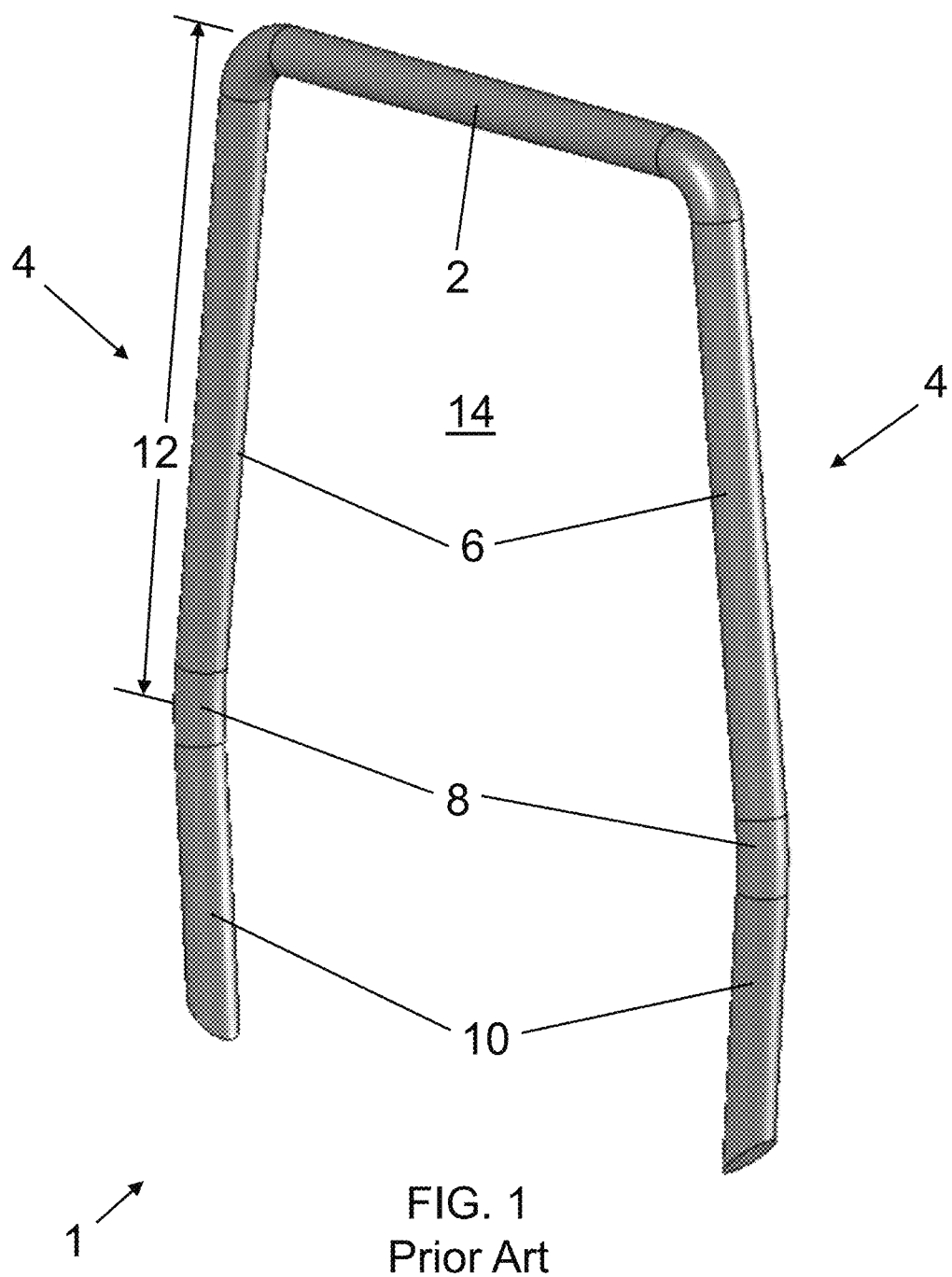
FIG. 1 is a perspective view from above a side of an exemplary prior art surgical staple.
Figure 2:
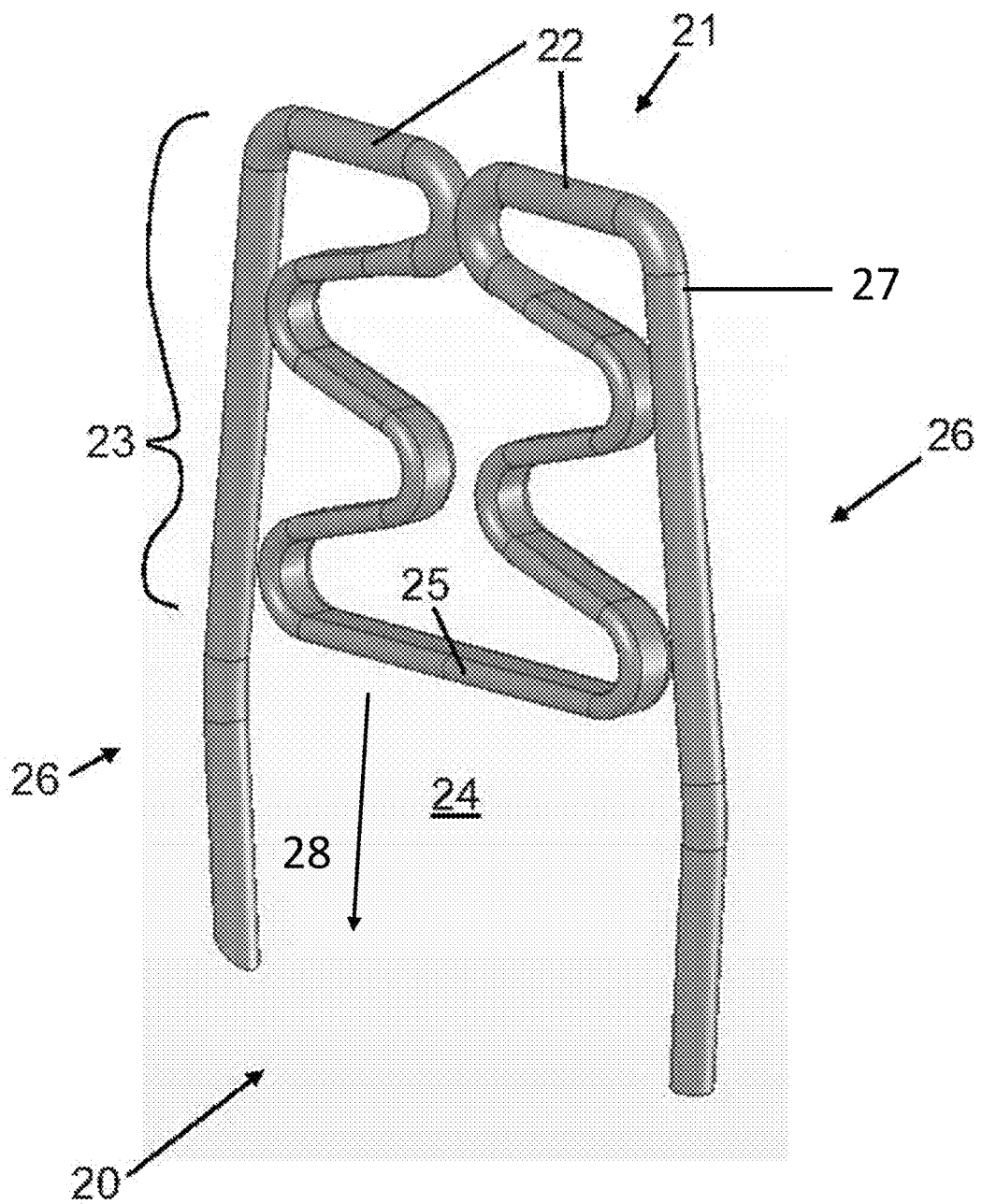
FIG. 2 is a perspective view from above a side of a first exemplary embodiment of an OTC staple according to the invention.

Referring now to the figures of the drawings in detail and first, particularly to FIG. 2 thereof, there is shown a first exemplary embodiment of an automatic optimal tissue compression (OTC) staple 20 according to the invention. In this first embodiment, the bridge 21 has a center bridge portion 22 and an extension 23 that substantially increases the overall length of the bridge 21—as compared to the bridge 2 of the staple 1 of FIG. 1. As the upper bridge portion 22 transitions into the extension 23, it curves into and within the central region 24 of the staple 20. This extension 23 can be in any shape or of any material so long as it delivers a pre-set compressive force to the tissue at a compressing portion 25, and as long as it allows for absorption (within the area between the compressing portion 25 and the upper bridge portion 22) of forces greater than this pre-set force. Therefore, the shape can be trapezoidal, triangular, sinusoidal, or any other configuration. An exemplary embodiment of relatively sinusoidal curves is shown in FIG. 2. These curves traverse two periods in the illustrated embodiment, however, the number of wave periods can be varied (smaller or larger). The extension 23 has two mirror-symmetrical portions each starting from the upper bridge portion 22 and ending at respective ends of the compressing portion 25. Further, it is noted that neither the extension 23 nor the compressing portion 25 directly contacts the legs 26 in this exemplary configuration.

In the embodiment of FIG. 2, the extension 26 and the compressing portion 29 are integral with the upper bridge portion 22 and a base end 27 of the legs 26. The legs 26 are shown as relatively circular in cross-section. The bridge 21 and all of the compressing components 22, 23, 25 can also be circular in cross-section. Alternatively, as shown in FIG. 2, any portion of the extension 23 and/or the compressing portion 25 can have different cross-sectional shapes, such as ovular, rectangular, or polygonal. In the embodiment shown, the cross-section of the extension 23 after the first curve away from the upper bridge portion 22 is shaped in a "racetrack" form (two relatively straight sides with two curved ends connecting each end of the sides). The upper bridge portion 22 can also have a different cross-sectional shape. The extension 23 and compressing portion 25 are, in this embodiment, even in cross-sectional area. Different portions of these parts can, however, have varying cross-sectional areas (i.e., varying thicknesses) as desired.

When the upper bridge 22, the extension 23, and the compressing portion 25 are shaped to deliver the pre-set compressive force to the tissue in a substantially longitudinal direction 28 of an unbent section of the leg portions 26 and to absorb forces greater than this pre-set force, the overall effect is to create an OTC device having a given spring coefficient. In other words, the OTC device maintains the preset compressive force within the stapled area even after tissue changes states, such as expanding due to swelling and/or contracting during desiccation. Variation of the cross-section of any portion of the upper bridge 22, the extension 23, and the compressing portion 25 will allow for different OTC spring coefficients and, therefore, allows for adjustment of the compressive and reactive force constants of the OTC device within the staple 20. Variation of the material making up all of the staple 20 or any of its portions also permits adjustment of the OTC force.

Figure 3:
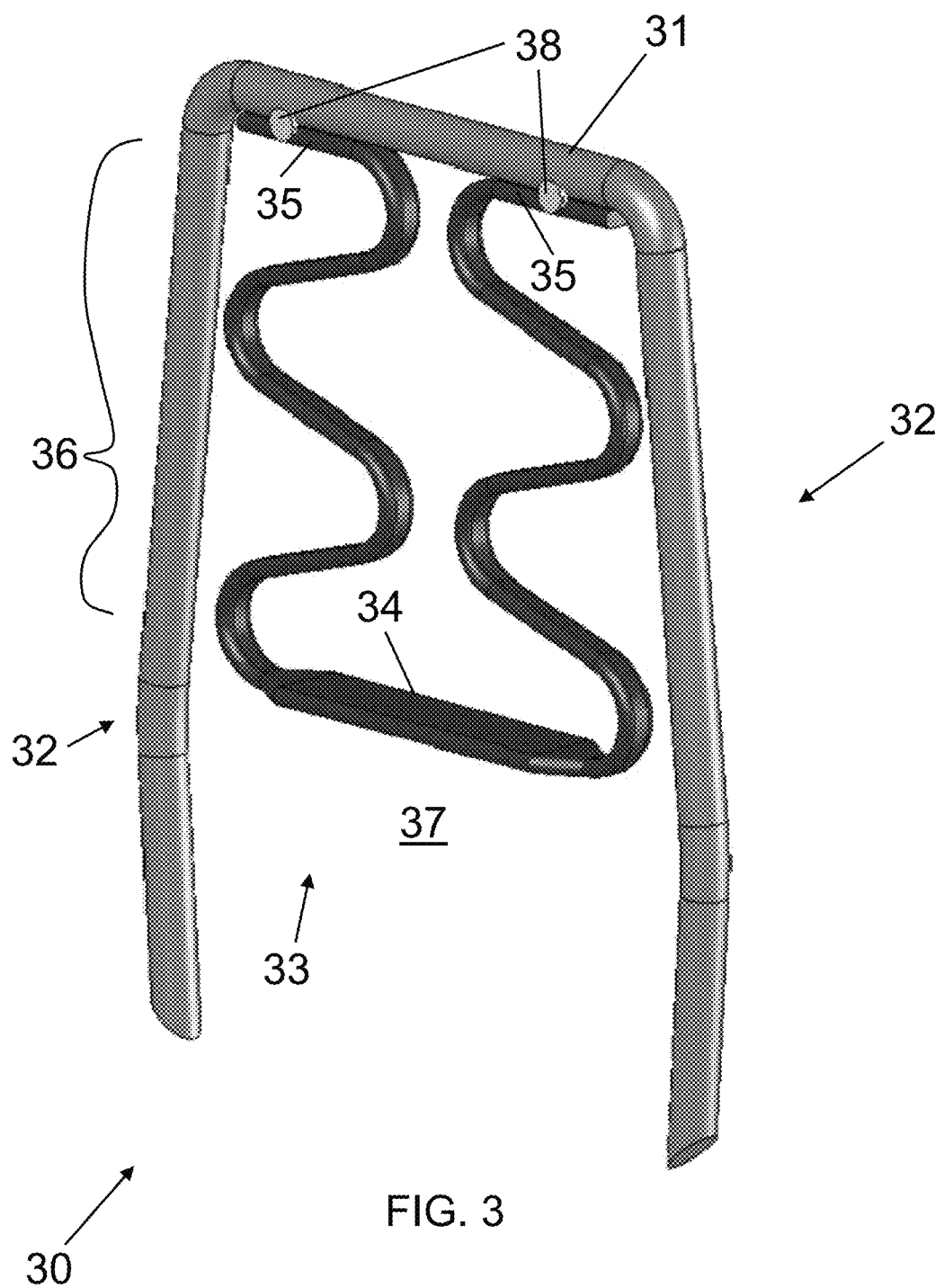
FIG. 3 is a perspective view from above a side of a second exemplary embodiment of an OTC staple according to the invention.

FIG. 3 illustrates a second exemplary embodiment of the OTC staple 30 according to the invention. In this variation, as compared to the embodiment of FIG. 2, the OTC portion is not integral with the bridge 31 and the legs 32. Instead, the OTC device 33 is separate therefrom and is connected to these staple portions. Specifically, the OTC device 33 has a compressing portion 34 that directly contacts the tissue being compressed and an extension 36 for providing the load-bearing force when tissue is compressed within the central region 37 of the staple 30. The OTC device 33 also has a connecting portion 35 for attaching the OTC device 33 to the bridge 31. The extension 36 connects the upper and lower portions 34, 35 of the OTC device 33. The extension 33 and the compressing portion 34 are, in this embodiment, different in cross-sectional area. Here, the cross-sectional area of the compressing portion 34 is wider than the extension 36. Any portions of the extension 33 or the compressing portion 34 can be varied to have same or varying cross-sectional areas (i.e., varying thicknesses).

Connection of the OTC device 33 to the staple, for example, at the bridge 31, can occur by any fastening measure. One exemplary connection method is spot welding, which is indicated in FIG. 3 by reference numeral 38. Other exemplary methods of attaching suitable materials together include soldering and brazing. The type or types of material of the staple portions 31, 32 and the OTC device 33 will direct a preferable attachment method. In the case of attaching two materials together that are not suited to be welded, soldered or brazed, other attachment methods can be used such as crimping and adhesive bonding. Features can be added to one or both of the two components to facilitate the crimp or bond. These features could be configured to have the components snap together. In the case of dissimilar materials, for example, if the staple material is stainless steel and the OTC device 33 is of nickel titanium alloy, then preferred attachment measures include crimping, adhesive bonding, or snapping.

In this second embodiment, the OTC device 33 behaves similar to the OTC portions of the embodiment of FIG. 2 and can be shaped with the same variations of cross-section and other spatial characteristics and can be formed with the same variations in material composition. Variation of any attribute of the OTC device 33 allows for adjustment of the compressive and reactive force constants thereof on the compressed tissue. The extension 36 can be any shape or material so long as it delivers a pre-set compressive force to the tissue at the compressing portion 34 and as long as it allows for absorption of forces greater than this pre-set force. An exemplary embodiment selected for this exemplary OTC device 33 is a relatively sinusoidal set of curves traversing less than two periods. The extension 36 has two mirror-symmetrical portions each starting from the bridge 31 and ending at respective ends of the compressing portion 34. In this exemplary embodiment, neither the extension 36 nor the compressing portion 34 directly contacts the legs 32. Most of the cross-section of the OTC device 33 has a racetrack form. Like the embodiment of FIG. 2, the cross-section can be varied in any desired way to deliver the pre-set compressive force to the tissue and to absorb forces greater than this pre-set force.

Figure 4:
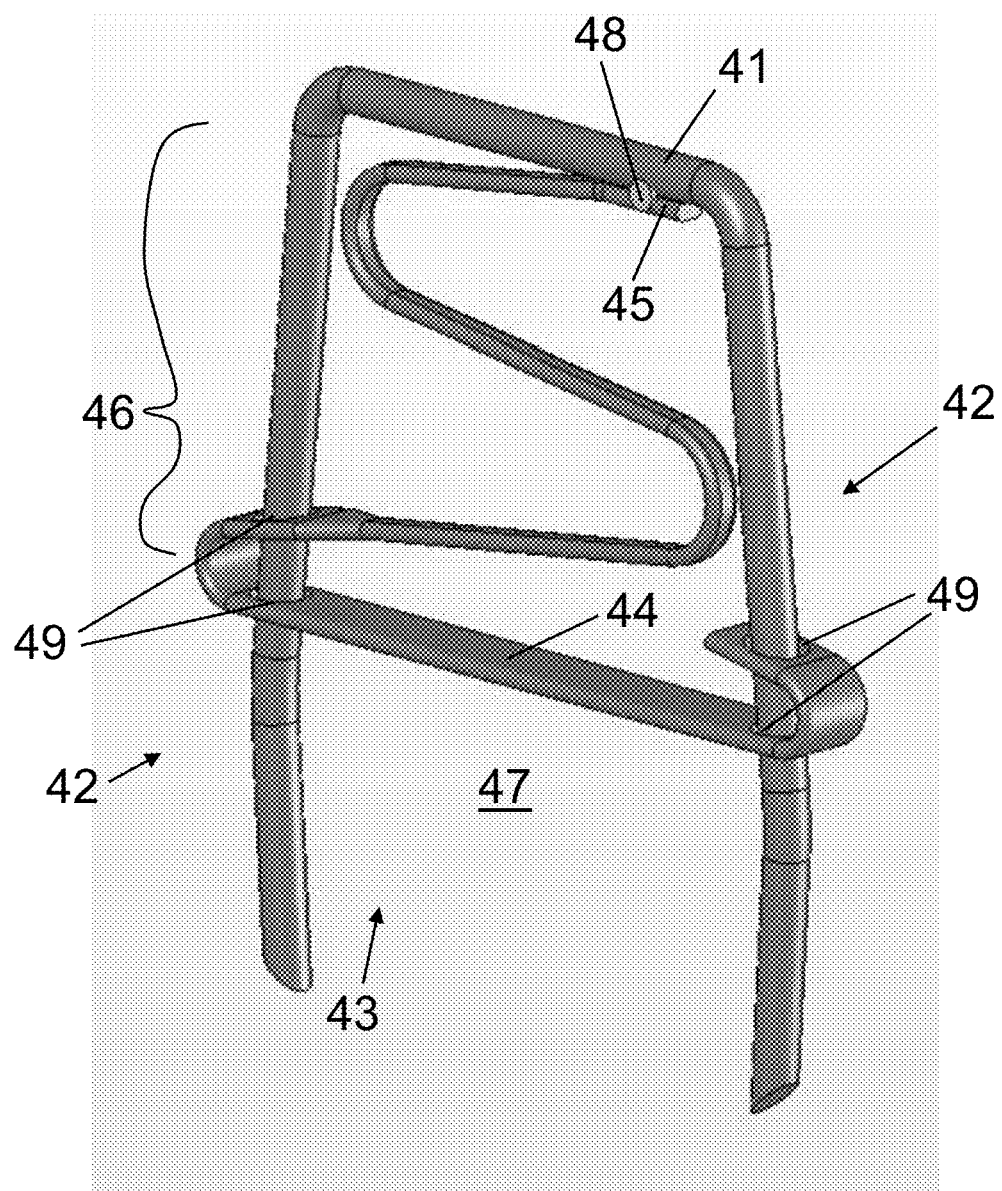
FIG. 4 is a perspective view from above a side of a third exemplary embodiment of an OTC staple according to the invention.

FIG. 4 illustrates a third exemplary embodiment of the OTC staple 40 according to the invention. In this variation, as compared to the embodiments of FIGS. 2 and 3, the OTC portion 43 is not symmetrical with respect to the bridge 41 or the legs 42. Also, like the embodiment of FIG. 3, the OTC portion is not integral with either the bridge 41 or the legs 42. The OTC device 43 is a separate part from the bridge 41 and the legs 42 and is fixedly connected to the bridge 41 at a connection location (for example, with a spot weld 48; other fixation/connection processes can be used). In particular, a connecting portion 45 of the OTC device 43 fixedly secures the OTC device 43 to the bridge 41. An extension 46 of the OTC device 43 provides the load-bearing force when tissue is compressed within the central region 47 of the staple 40 and a compressing portion 44 directly contacts the tissue being compressed.

Notably different from the embodiments of FIGS. 2 and 3 is the compressing portion 44. Here, the width of the compressing portion 44 (defined along the line between the two legs 42 of the staple 40) is greater than the separation distance of the two legs 42. The compressing portion 44 is provided with orifices 49 having a shape substantially corresponding to the cross-sectional shape of the upper portion of the staple legs 42 but slightly larger. The legs 42 pass through and slidably rest within these orifices 49. In such a configuration, movement of the OTC device 43 out of the bridge-legs plane is substantially prevented. Because the orifices 49 are shaped to be slightly larger than the cross-section of the legs 42, the extension 46 acts as a compression spring in the bridge-legs plane as the compressing portion 44 moves up and down along the upper portion of the legs 42 (up being defined as the direction towards the bridge 41 from the piercing tips of the legs 42). Thus, the OTC device 43 of the third embodiment behaves different from the OTC devices of FIGS. 2 and 3 because of the form-locking and sliding connection between the connecting portion 44 and the legs 42. A form-locking connection is one that connects two elements together due to the shape of the elements themselves, as opposed to a force-locking connection, which locks the elements together by force external to the elements.

Like the previous embodiments, the OTC device 43 can be shaped with variations in cross-section and other spatial characteristics and can be formed with a variety of material compositions. The extension 46 and compressing portion 44 are, in this embodiment, different in cross-sectional area. Here, the cross-sectional area of the compressing portion 44 is wider than the extension 46. Any portions of the extension 46 or the compressing portion 44 can be varied to have same or varying cross-sectional areas (i.e., varying thicknesses). The extension 46 can be any shape or material so long as it delivers the pre-set compressive force to the tissue at the compressing portion 44 and as long as it allows for absorption of forces greater than this pre-set force. An exemplary embodiment selected for this OTC device 43 is a relatively sinusoidal curve traversing approximately one sinusoidal period. Virtually all of the cross-section of the OTC device 43 has a racetrack form, but can be changed as desired to other shapes (e.g., circular, ovular, polygonal, etc.). As described above, variation of any attribute of the OTC device 43 allows for adjustment of the compressive and reactive force constants thereof on the compressed tissue in the central region 47.

Figure 5:
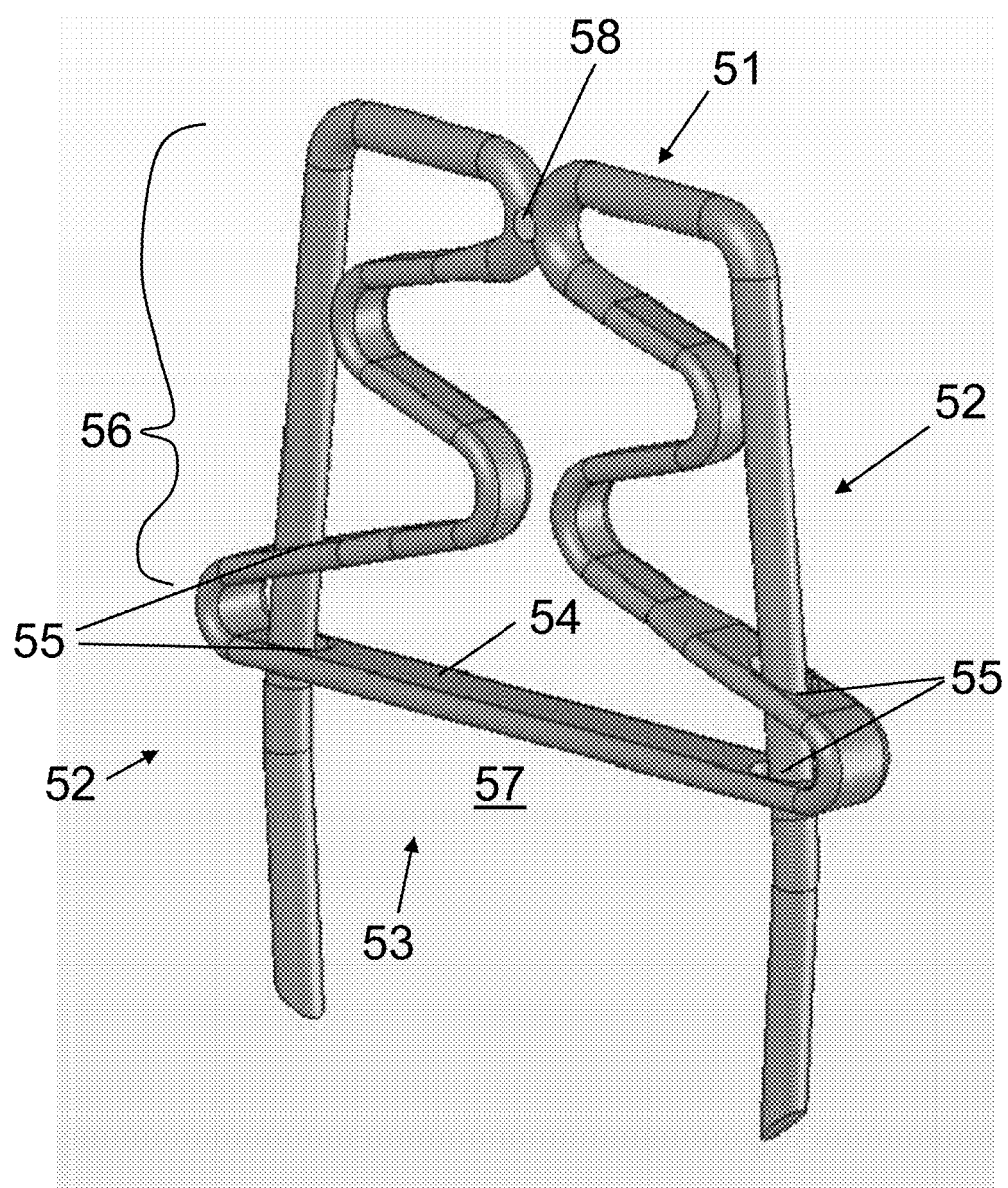
FIG. 5 is a perspective view from above a side of a fourth exemplary embodiment of an OTC staple according to the invention.

FIG. 5 illustrates a fourth exemplary embodiment of the OTC staple 50 according to the invention. This variation has some of the features of the above embodiments. In this variant, like the embodiment of FIG. 2, the OTC portion is symmetrical with respect to the bridge 51 and the legs 52 and the OTC device 53 is integral with the bridge 51. Like the embodiment of FIG. 4, the compressing portion 54 has a width greater than the separation distance of the two legs 52 and has ports 55 with a shape substantially corresponding to the cross-sectional shape of the upper portion of the legs 52, but slightly larger. The legs 52 pass through these ports 55. In this configuration, movement of the OTC device 53 out of the bridge-legs plane is substantially prevented. The extension 56 of the OTC device 53 traverses from the bridge 51 to the compressing portion 54. Because the ports 55 are shaped to be slightly larger than the cross-section of the legs 52, the extension 56 acts as a compression spring in the bridge-legs plane as the compressing portion 54 moves up and down along the upper portion of the legs 52. It is the extension 56 that provides the load-bearing force when tissue is compressed within the central region 57 of the staple 50. Because of the form-locking and sliding connection between the compressing portion 54 and the legs 52, the OTC device 53 of the fourth embodiment behaves similar to the OTC devices of FIG. 4.

Here, the OTC device 53 is integral with the legs 52, the bridge 51, and the compressing portion 54. Because the two sides of the bridge 51 are not integral, they can separate from one another when the staple 50 is subjected to a twisting force. If desired, to substantially prevent such separation, the central portions of the bridge 51 can be fixedly connected to one another at a connection location (for example, with a spot weld 58; other connection processes can be used as well).

Like the previous embodiments, the OTC device 53 can be shaped with variations in cross-section and other spatial characteristics and can be formed with a variety of material compositions. Any portions of the extension 56 or the compressing portion 54 can be varied to have the same or varying cross-sectional areas (i.e., varying thicknesses). The extension 56 and compressing portion 54 are, in this embodiment, different in cross-sectional areas. Here, the cross-sectional area of the upper majority of the extension 56 is narrower than the lower portion of the extension 56 and the cross-section of the lower portion of the extension 56 gradually increases in width until it is equal to the cross-section of the compressing portion 54.

The extension 56 can be any shape or material so long as it delivers the pre-set compressive force to the tissue at the compressing portion 54 and as long as it allows for absorption of forces greater than this pre-set force. An exemplary embodiment selected for this OTC device 53 is a relatively sinusoidal curve traversing more than one sinusoidal period. Again, only for illustrative purposes, the cross-section of the OTC device 53 has a racetrack shape, but can be changed as desired to other shapes (e.g., circular, ovular, polygonal, etc.). As described above, variation of any attribute of the OTC device 53 allows for adjustment of the compressive and reactive force constants thereof on the compressed tissue in the central region 57.

Figure 6:
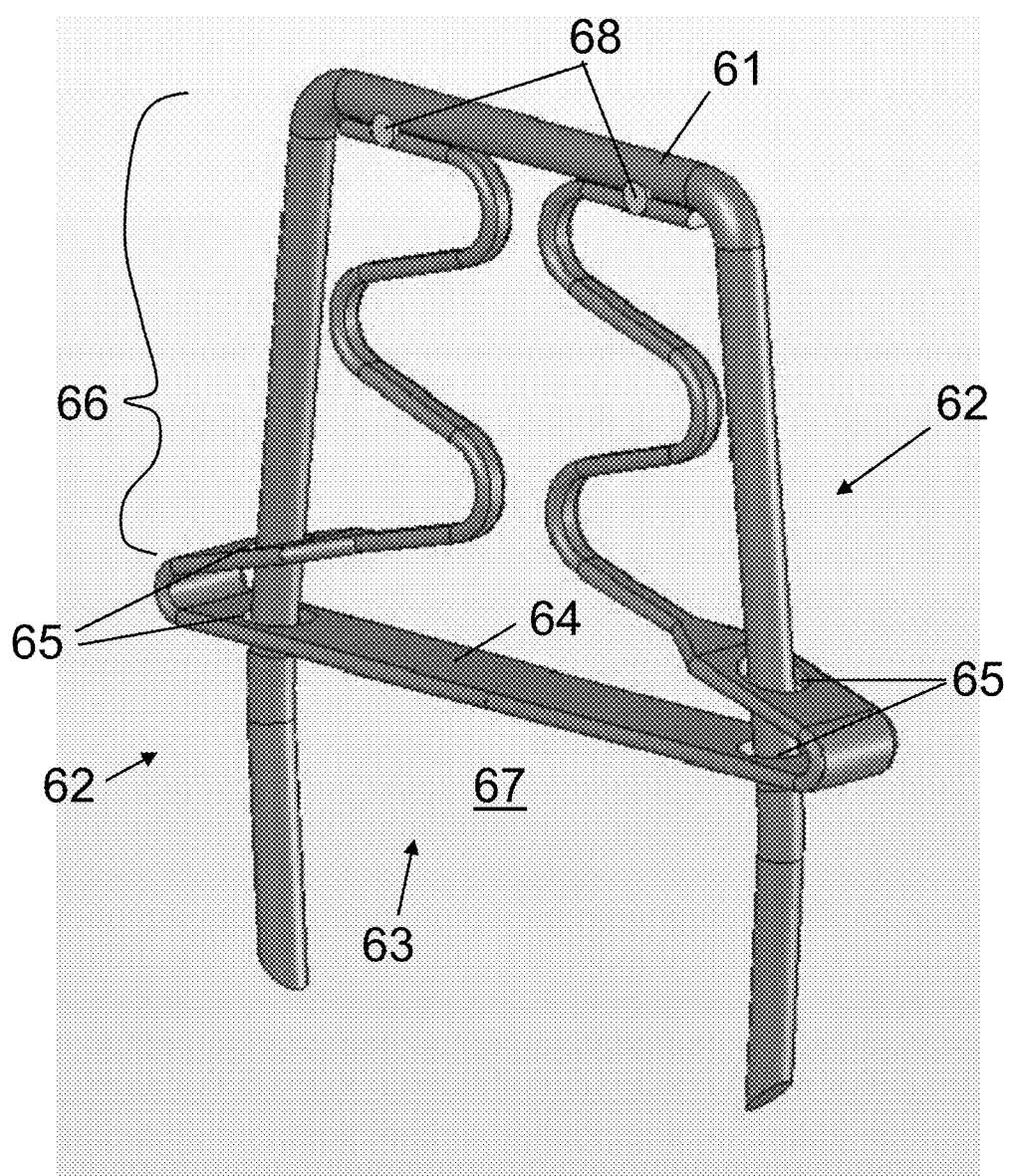
FIG. 6 is a perspective view from above a side of a fifth exemplary embodiment of an OTC staple according to the invention.

FIG. 6 illustrates a fifth exemplary embodiment of the OTC staple 60 according to the invention. This variation has some of the features of the above embodiments. In this variant, like the embodiment of FIG. 3, the OTC portion is symmetrical with respect to the bridge 61 and the legs 62 and the OTC device 63 is a separate part from the bridge 61 and legs 62 of the staple 60. Like the embodiment of FIGS. 4 and 5, the compressing portion 64 has a width greater than the separation distance of the two legs 62 and has ports 65 with a shape substantially corresponding to the cross-sectional shape of the upper portion of the legs 62, but slightly larger. The legs 62 pass through these ports 65. In this configuration, movement of the OTC device 63 out of the bridge-legs plane is substantially prevented. The extension 66 of the OTC device 63 traverses from the bridge 61 to the compressing portion 64. Because the ports 65 are shaped to be slightly larger than the cross-section of the legs 62, the extension 66 acts as a compression spring in the bridge-legs plane as the compressing portion 64 moves up and down along the upper portion of the legs 62. It is the extension 66 that provides the load-bearing force when tissue is compressed within the central region 67 of the staple 60. Because of the form-locking and sliding connection between the compressing portion 64 and the legs 62, the OTC device 63 of the fifth embodiment behaves similar to the OTC devices of FIGS. 4 and 5.

Connection of the OTC device 63 to the staple 60, for example, at the bridge 61, can occur by any fastening measure. One exemplary connection method is spot welding, which is indicated in FIG. 6 by reference numeral 68. The type or types of material of the staple portions 61, 62 and the OTC device 63 will direct a preferable attachment method. In the case of attaching two materials together that are not suited to be welded, soldered or brazed, other attachment methods can be used such as crimping and adhesive bonding. Features can be added to one or both of the two components to facilitate the crimp or bond. These features could be configured to have the components snap together. In the case of dissimilar materials, for example, if the staple material is stainless steel and the OTC device 63 is of nickel titanium alloy, then preferred attachment measures include crimping, adhesive bonding, or snapping.

Like the previous embodiments, the OTC device 63 can be shaped with variations in cross-section and other spatial characteristics and can be formed with a variety of material compositions. Any portions of the extension 66 or the compressing portion 64 can be varied to have the same or different cross-sectional areas (i.e., varying thicknesses). The extension 66 and compressing portion 64 are, in this embodiment, different in cross-sectional areas. Here, the cross-sectional area of most of the extension 66 is narrower than the lowermost portion of the extension 66 and the cross-section of this lowermost portion of the extension 66 gradually increases in width until it is equal to the cross-section of the compressing portion 64, which is substantially wider.

The extension 66 can be any shape or material so long as it delivers the pre-set compressive force to the tissue at the compressing portion 64 and as long as it allows for absorption of forces greater than this pre-set force. An exemplary embodiment selected for this OTC device 63 is a relatively sinusoidal curve traversing more than one sinusoidal period. Again, only for illustrative purposes, the cross-section of the OTC device 63 has a racetrack shape, but can be changed as desired to other shapes (e.g., circular, ovular, polygonal, etc.). As described above, variation of any attribute of the OTC device 63 allows for adjustment of the compressive and reactive force constants thereof on the compressed tissue in the central region 67.

Figure 7:
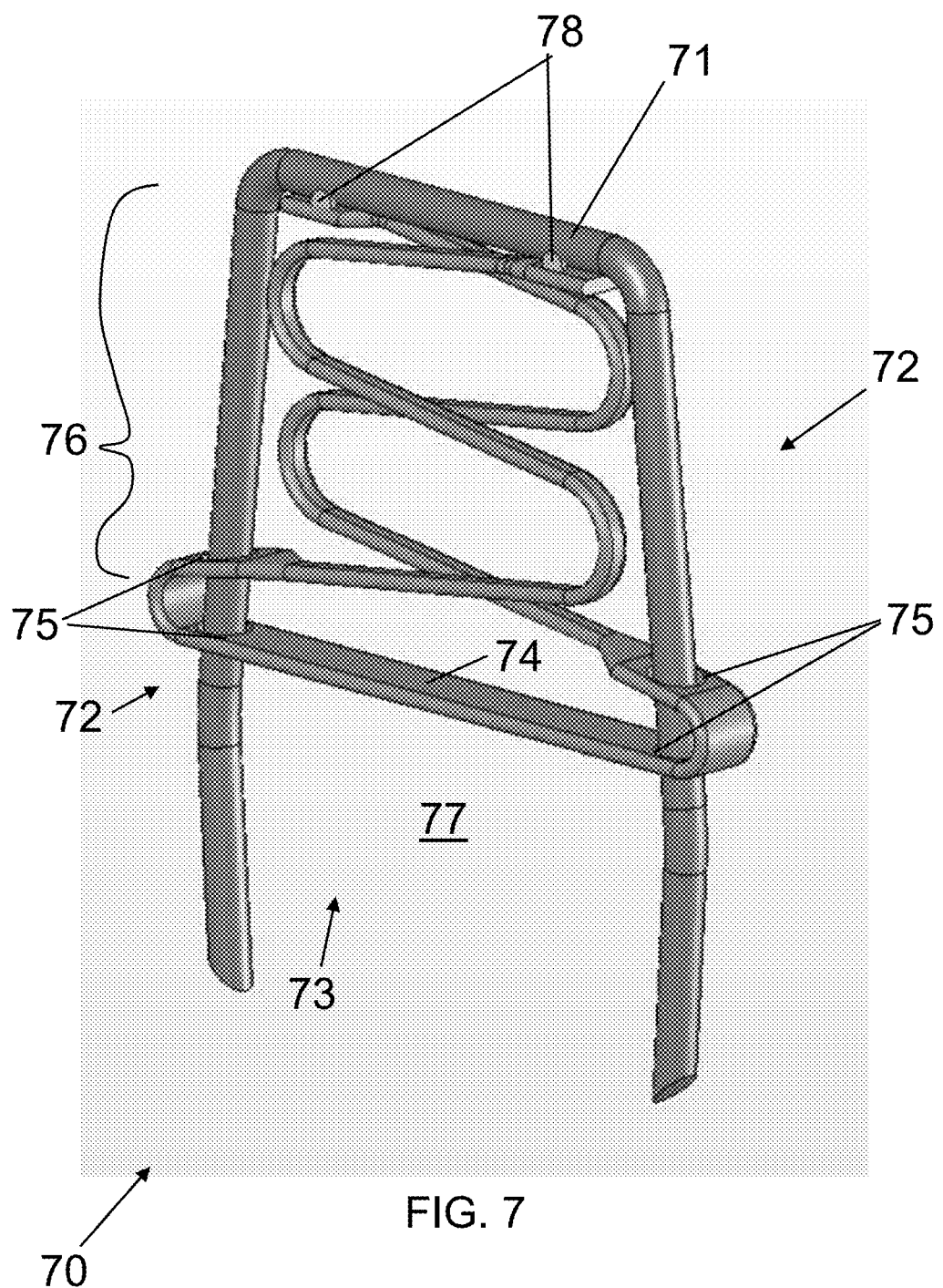
FIG. 7 is a perspective view from above a side of a sixth exemplary embodiment of an OTC staple according to the invention.

FIG. 7 illustrates a sixth exemplary embodiment of the OTC staple 70 according to the invention. This variation has some of the features of the above embodiments. In this variant, like the embodiment of FIG. 3, the OTC portion is symmetrical with respect to the bridge 71 and the legs 72 and the OTC device 73 is a separate part from the bridge 71 and legs 72 of the staple 70. Like the embodiment of FIGS. 4 to 6, the compressing portion 74 has a width greater than the separation distance of the two legs 72 and has ports 75 with a shape substantially corresponding to the cross-sectional shape of the upper portion of the legs 72, but slightly larger. The legs 72 pass through these ports 75. In this configuration, movement of the OTC device 73 out of the bridge-legs plane is substantially prevented. The extension 76 of the OTC device 73 traverses from the bridge 71 to the compressing portion 74. Because the ports 75 are shaped to be slightly larger than the cross-section of the legs 72, the extension 76 acts as a compression spring in the bridge-legs plane as the compressing portion 74 moves up and down along the upper portion of the legs 72. It is the extension 76 that provides the load-bearing force when tissue is compressed within the central region 77 of the staple 70. Because of the form-locking and sliding connection between the compressing portion 74 and the legs 72, the OTC device 73 of the sixth embodiment behaves similar to the OTC devices of FIGS. 4 to 6.

Connection of the OTC device 73 to the staple 70, for example, at the bridge 71, can occur by any fastening measure. One exemplary connection method is spot welding, which is indicated in FIG. 7 by reference numeral 78. The type or types of material of the staple portions 71, 72 and the OTC device 73 will direct a preferable attachment method. In the case of attaching two materials together that are not suited to be welded, soldered or brazed, other attachment methods can be used such as crimping and adhesive bonding. Features can be added to one or both of the two components to facilitate the crimp or bond. These features could be configured to have the components snap together. In the case of dissimilar materials, for example, if the staple material is stainless steel and the OTC device 73 is of nickel titanium alloy, then preferred attachment measures include crimping, adhesive bonding, or snapping.

It is noted that the extensions (i.e., springs) in each of FIGS. 2, 3, 5, and 6 are in the same plane, which can be the bridge-legs plane (as shown) or out of that plane. In comparison to these embodiments, the extension 76 has the springs residing in different planes (i.e., one next to the other.

Like the previous embodiments, the OTC device 73 can be shaped with variations in cross-section and other spatial characteristics and can be formed with a variety of material compositions. Any portions of the extension 76 or the compressing portion 74 can be varied to have the same or varying cross-sectional areas (i.e., varying thicknesses). The extension 76 and the compressing portion 74 are, in this embodiment, different in cross-sectional areas. Here, the cross-sectional area of most of the extension 76 is narrower than the lowermost portion of the extension 76 and the cross-section of this lowermost portion of the extension 76 gradually increases in width until it is equal to the cross-section of the compressing portion 74, which is substantially wider.

The extension 76 can be any shape or material so long as it delivers the pre-set compressive force to the tissue at the compressing portion 74 and as long as it allows for absorption of forces greater than this pre-set force. An exemplary embodiment selected for this OTC device 73 is a relatively sinusoidal curve traversing more than one sinusoidal period. Again, only for illustrative purposes, the cross-section of the OTC device 73 has a racetrack shape, but can be changed as desired to other shapes (e.g., circular, ovular, polygonal, etc.). As described above, variation of any attribute of the OTC device 73 allows for adjustment of the compressive and reactive force constants thereof on the compressed tissue in the central region 77.

Figure 8:
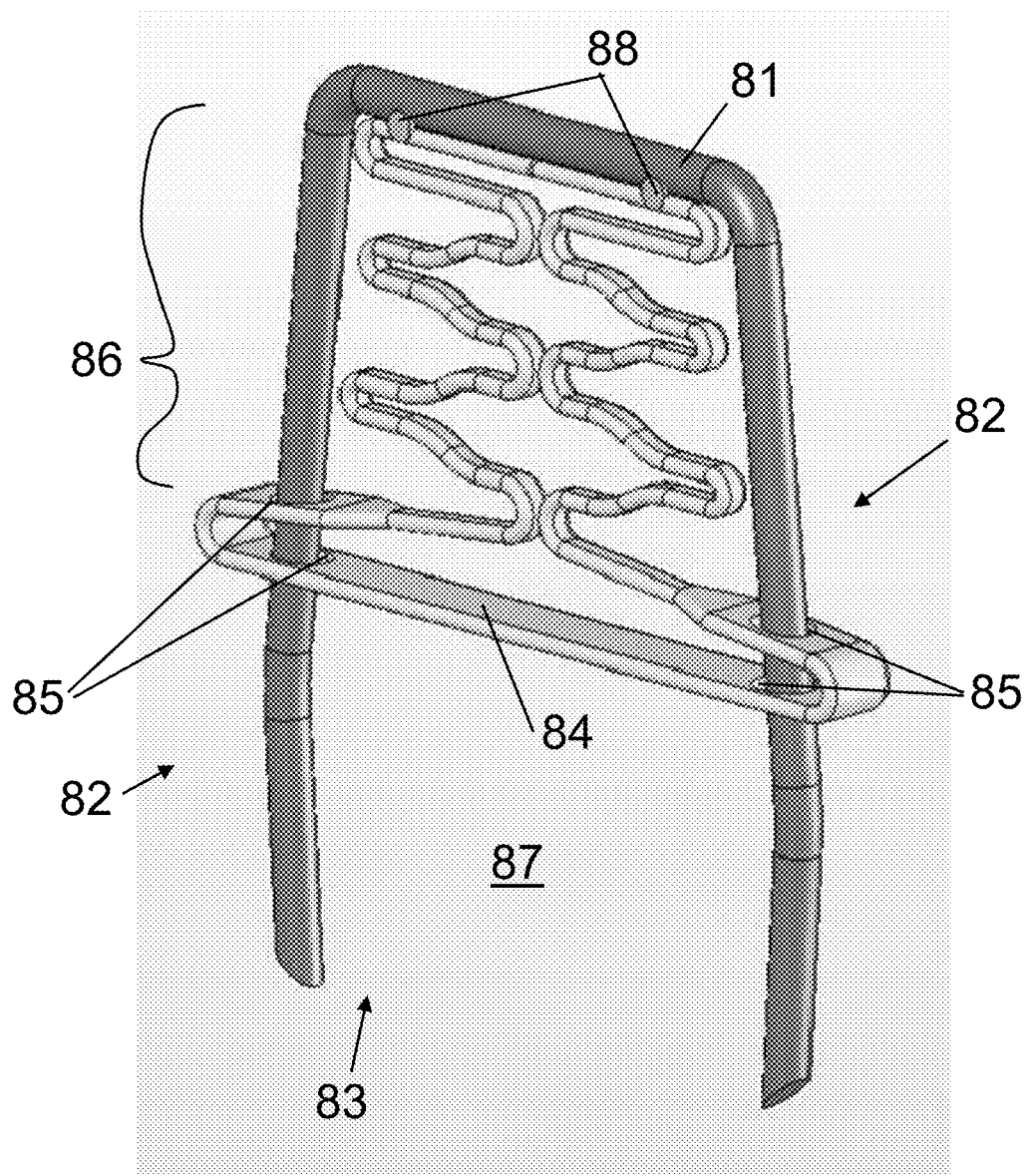
FIG. 8 is a perspective view from above a side of a seventh exemplary embodiment of an OTC staple according to the invention.

FIG. 8 illustrates a seventh exemplary embodiment of the OTC staple 80 according to the invention. This variation has some of the features of the above embodiments. In this variant, like the embodiment of FIG. 3, the OTC portion is symmetrical with respect to the bridge 81 and the legs 82, and the OTC device 83 is a separate part from the bridge 81 and legs 82 of the staple 80. Like the embodiment of FIGS. 4 to 7, the compressing portion 84 has a width greater than the separation distance of the two legs 82 and has ports 85 with a shape substantially corresponding to the cross-sectional shape of the upper portion of the legs 82, but slightly larger. The legs 82 pass through these ports 85. In this configuration, movement of the OTC device 83 out of the bridge-legs plane is substantially prevented. The extension 86 of the OTC device 83 traverses from the bridge 81 to the compressing portion 84. Because the ports 85 are shaped to be slightly larger than the cross-section of the legs 82, the extension 86 acts as a compression spring in the bridge-legs plane as the compressing portion 84 moves up and down along the upper portion of the legs 82. It is the extension 86 that provides the load-bearing force when tissue is compressed within the central region 87 of the staple 80. Because of the form-locking and sliding connection between the compressing portion 84 and the legs 82, the OTC device 83 of the seventh embodiment behaves similar to the OTC devices of FIGS. 4 to 7.

Like the previous embodiments, the OTC device 83 can be shaped with variations in cross-section and other spatial characteristics and can be formed with a variety of material compositions. Any portions of the extension 86 or the compressing portion 84 can be varied to have the same or varying cross-sectional areas (i.e., varying thicknesses). The extension 86 and the compressing portion 84 are, in this embodiment, different in cross-sectional areas. Here, the cross-sectional area of most of the extension 86 is smaller and narrower than the lowermost portion of the extension 86 and the cross-section of this lowermost portion gradually increases in width until it is equal to the cross-section of the compressing portion 84, which is substantially wider. Also, the cross-sectional area of this extension 86 is smaller than previous embodiments (but it need not be).

The extension 86 can be any shape or material so long as it delivers the pre-set compressive force to the tissue at the compressing portion 84 and as long as it allows for absorption of forces greater than this pre-set force. An exemplary embodiment selected for this OTC device 83 is a relatively sinusoidal curve traversing a more than two periods and also having a second "interior" curve that traverses sinusoidal periods. In this embodiment, the OTC device 83 has an uppermost portion that is, in contrast to the embodiments of FIGS. 3, 6, and 7 a single bar extending along a majority of the bridge 81.

Connection of the OTC device 83 to the staple 80, for example, at the bridge 81, can occur by any fastening measure. One exemplary connection method is spot welding, which is indicated in FIG. 8 by reference numeral 88. Because there is contact over most of the bridge 81, the OTC device 83 can be welded over the entire length thereof. The type or types of material of the staple portions 81, 82 and the OTC device 83 will direct a preferable attachment method. In the case of attaching two materials together that are not suited to be welded, soldered or brazed, other attachment methods can be used such as crimping and adhesive bonding. Features can be added to one or both of the two components to facilitate the crimp or bond. These features could be configured to have the components snap together. In the case of dissimilar materials, for example, if the staple material is stainless steel and the OTC device 83 is of nickel titanium alloy, then preferred attachment measures include crimping, adhesive bonding, or snapping.

Only for illustrative purposes, the cross-section of the OTC device 83 has a racetrack shape, but can be changed as desired to other shapes (e.g., circular, ovular, polygonal, etc.). As described above, variation of any attribute of the OTC device 83 allows for adjustment of the compressive and reactive force constants thereof on the compressed tissue in the central region 87.

Figure 9:
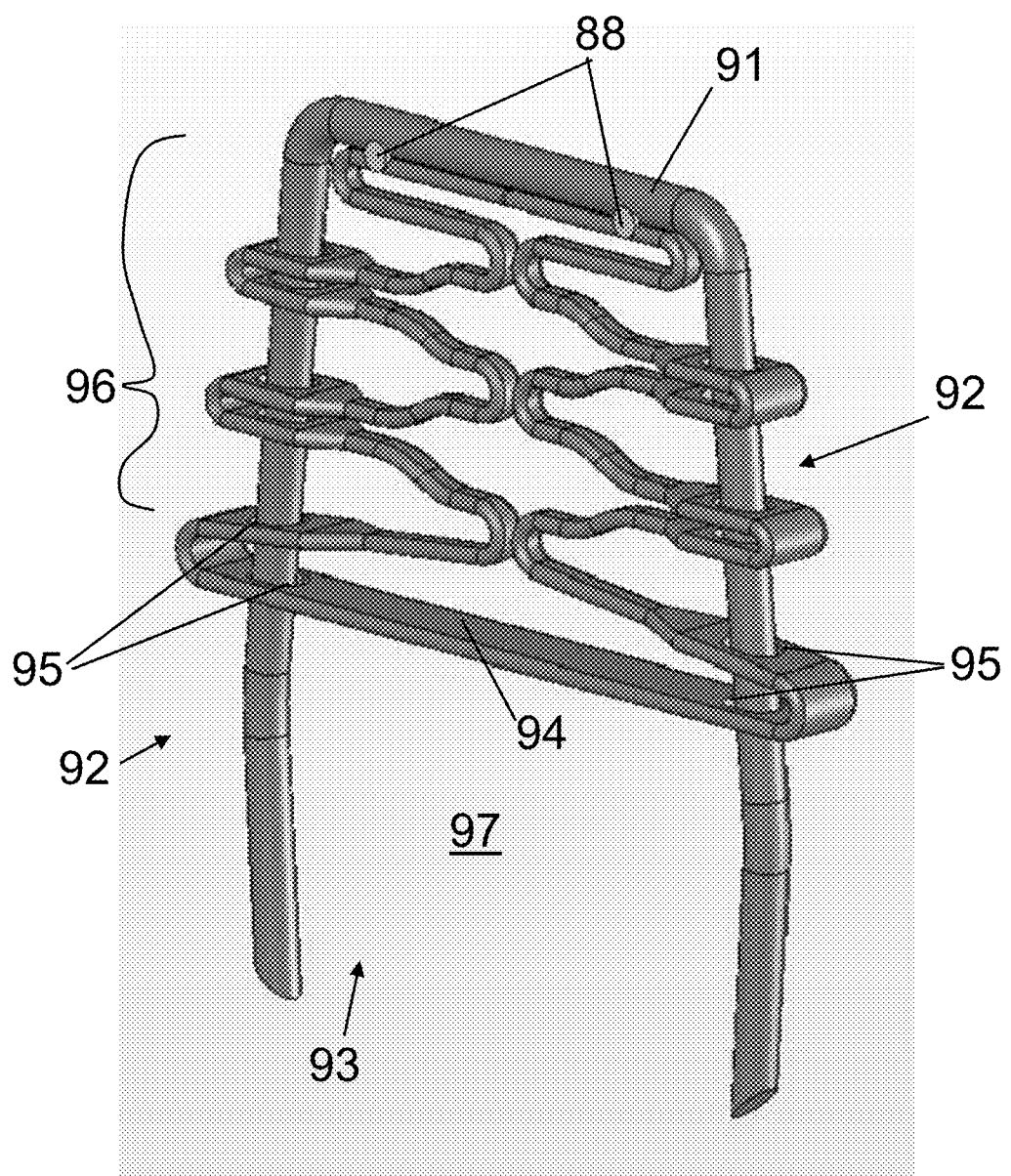
FIG. 9 is a perspective view from above a side of an eighth exemplary embodiment of an OTC staple according to the invention.

FIG. 9 illustrates an eighth exemplary embodiment of the OTC staple 90 according to the invention. This variation has some of the features of the above embodiments. In this variant, like the embodiment of FIG. 3, the OTC portion is symmetrical with respect to the bridge 91 and the legs 92, and the OTC device 93 is a separate part from the bridge 91 and legs 92 of the staple 90. Like the embodiment of FIGS. 4 to 8, the compressing portion 94 has a width greater than the separation distance of the two legs 92 and has ports 95 with a shape substantially corresponding to the cross-sectional shape of the upper portion of the legs 92, but slightly larger. The legs 92 pass through these ports 95. In this configuration, movement of the OTC device 93 out of the bridge-legs plane is substantially prevented. The extension 96 of the OTC device 93 traverses from the bridge 91 to the compressing portion 94. Because the ports 95 are shaped to be slightly larger than the cross-section of the legs 92, the extension 96 acts as a compression spring in the bridge-legs plane as the compressing portion 94 moves up and down along the upper portion of the legs 92. It is the extension 96 that provides the load-bearing force when tissue is compressed within the central region 97 of the staple 90. Because of the form-locking and sliding connection between the compressing portion 94 and the legs 92, the OTC device 93 of the eighth embodiment behaves similar to the OTC devices of FIGS. 4 to 8.

Like the previous embodiments, the OTC device 93 can be shaped with variations in cross-section and other spatial characteristics and can be formed with a variety of material compositions. Any portion(s) of the extension 96 or the compressing portion 94 can be varied to have the same or varying cross-sectional areas (i.e., varying thicknesses). The extension 96 and the compressing portion 94 are, in this embodiment, different in cross-sectional areas. Here, the cross-sectional area of most of the extension 96 is smaller and narrower than the lowermost portion of the extension 96 and the cross-section of this lowermost portion gradually increases in width until it is equal to the cross-section of the compressing portion 94, which is substantially wider. Also, the cross-sectional area of this extension 96 is smaller than previous embodiments (but need not be). With such a relatively smaller cross-sectional shape, the curves of the extension 96 might tend to deform or move out of the bridge-legs plane, which tendency can increase or decrease depending upon the material of the extension 96. To prevent such deformation and/or movement, a plurality of guiding tabs 99 are disposed at one or more of the outside ends of each periodic curve adjacent the legs 92. These guiding tabs 99 are shaped in a similar manner to the ends of the compressing portion 94, in that they have ports with a cross-sectional shape substantially corresponding to the cross-sectional shape of the upper portion of the legs 92 but slightly larger. The embodiment illustrated in FIG. 9 provides each guiding tab 99 with two relatively parallel plates each having one of the two ports through which the respective leg 92 is disposed. Like the lower portion of the extension 96, the cross-sectional area of the extension gradually increases in width until it is equal to the larger cross-section of the plate of the guiding tab 99. Another alternative of the guiding tab 99 is to have only a single plate with a single port. In such an embodiment (assuming the material was the same as a dual-plate embodiment), the curves of the extension 96 would be slightly stiffer because of the absence of the exterior curve of the guiding tab 99.

The extension 96 can be any shape or material so long as it delivers the pre-set compressive force to the tissue at the compressing portion 94 and as long as it allows for absorption of forces greater than this pre-set force. An exemplary embodiment selected for this OTC device 93 is a relatively sinusoidal curve having a second interior curve that traverses a few sinusoidal periods and, in this embodiment, has an uppermost portion that is, like the embodiment of FIG. 8, a single bar extending along a majority of the bridge 91. Connection of the OTC device 93 to the staple 90, for example, at the bridge 91, can occur by any fastening measure. One exemplary connection method is spot welding, which is indicated in FIG. 9 by reference numeral 98. Alternatively, the weld can be over the entire span contacting the bridge 91. The type or types of material of the staple portions 91, 92 and the OTC device 93 will direct a preferable attachment method. In the case of attaching two materials together that are not suited to be welded, soldered or brazed, other attachment methods can be used such as crimping and adhesive bonding. Features can be added to one or both of the two components to facilitate the crimp or bond. These features could be configured to have the components snap together. In the case of dissimilar materials, for example, if the staple material is stainless steel and the OTC device 93 is of nickel titanium alloy, then preferred attachment measures include crimping, adhesive bonding, or snapping.

Again, only for illustrative purposes, the cross-section of the OTC device 93 has a racetrack shape, but can be changed as desired to other shapes (e.g., circular, ovular, polygonal, etc.). As described above, variation of any attribute of the OTC device 93 allows for adjustment of the compressive and reactive force constants thereof on the compressed tissue in the central region 97.

Figure 10:
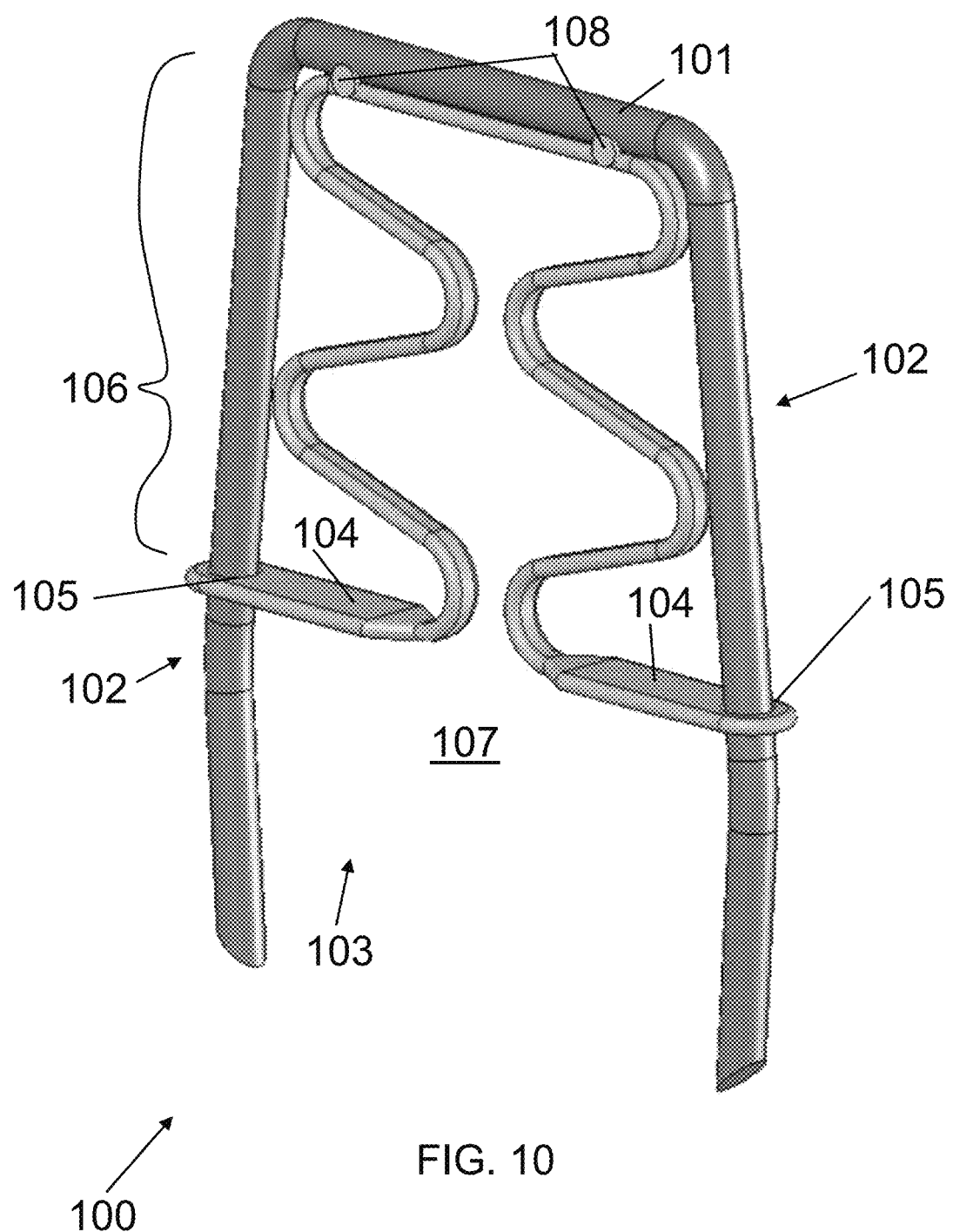
FIG. 10 is a perspective view from above a side of a ninth exemplary embodiment of an OTC staple according to the invention.

FIG. 10 illustrates a ninth exemplary embodiment of the OTC staple 100 according to the invention. This variation has some of the features of the above embodiments. In this variant, like the embodiment of FIG. 3, the OTC portion is symmetrical with respect to the bridge 101 and the legs 102, and the OTC device 103 is a separate part from the bridge 101 and legs 102 of the staple 100. The compressing portion 104, however, is unlike all of the previous embodiments. Here, the compressing portion 104 is formed from two compressing plates, each of these plates being attached to a respective lower end of two halves of the OTC device 103. The shape of the compressing portion 104 need not be a plate. It can be cylindrical, for example. Like previous embodiments, the lowermost end of the extension 106 gradually increases in cross-section until it is equal to the compressing portion 104. Each compressing plate, then, extends towards a respective one of the legs 102 and defines a respective port 105 for receiving therein the leg 102. The port 105 has a shape substantially corresponding to the cross-sectional shape of the upper portion of the legs 102, but is slightly larger. The legs 102 pass through each port 105 to form the OTC device 103. In this configuration, movement of the OTC device 103 out of the bridge-legs plane is substantially prevented. The extension 106 of the OTC device 103 traverses from the bridge 101 to the plates of the compressing portion 104. Because the ports 105 are shaped to be slightly larger than the cross-section of the legs 102, the extension 106 acts as a compression spring in the bridge-legs plane as the compressing portion 104 moves up and down along the upper portion of the legs 102. It is the extension 106 that provides the load-bearing force when tissue is compressed within the central region 107 of the staple 100.

In this embodiment, as compared to previous OTC device embodiments, the two sides of the OTC device 103 move independent from one another. Thus, if tissue varies in any characteristic within the central portion 107 (e.g., hardness, thickness, density), the optimal tissue compression force can be delivered independently and differently for each of the two differing tissue segments contacting the respective one of the sides of the OTC device 103.

Connection of the OTC device 103 to the staple 100, for example, at the bridge 101, can occur by any fastening measure. One exemplary connection method is spot welding, which is indicated in FIG. 10 by reference numeral 108. As the upper portion contacts almost all of the bridge 101, the weld 108, instead, can span any amount of the bridge 101. The type or types of material of the staple portions 101, 102 and the OTC device 103 will direct a preferable attachment method. In the case of attaching two materials together that are not suited to be welded, soldered or brazed, other attachment methods can be used such as crimping and adhesive bonding. Features can be added to one or both of the two components to facilitate the crimp or bond. These features could be configured to have the components snap together. In the case of dissimilar materials, for example, if the staple material is stainless steel and the OTC device 103 is of nickel titanium alloy, then preferred attachment measures include crimping, adhesive bonding, or snapping.

Like the previous embodiments, the OTC device 103 can be shaped with variations in cross-section and other spatial characteristics and can be formed with a variety of material compositions. Any portions of the extension 106 or the compressing portion 104 can be varied to have the same or varying cross-sectional areas (i.e., varying thicknesses). The extension 106 and the plates of the compressing portion 104 are, in this embodiment, different in cross-sectional areas. Here, the cross-sectional area of most of the extension 106 is smaller and narrower than the lowermost portion of the extension 86 and the cross-section of this lowermost portion gradually increases in width until it is equal to the cross-section of the respective plate of the compressing portion 104, which is substantially wider.

The extension 106 can be any shape or material so long as it delivers the pre-set compressive force to the tissue at the compressing portion 104 and as long as it allows for absorption of forces greater than this pre-set force. An exemplary embodiment selected for this OTC device 103 is a relatively sinusoidal curve having almost two sinusoidal periods and, in this embodiment, has an uppermost portion that is (like the embodiments of FIGS. 8 and 9) a single bar extending along a majority of the bridge 101. For illustrative purposes, the cross-section of the OTC device 103 has an ovular shape, but can be changed as desired to other shapes (e.g., circular, racetrack, polygonal, etc.). As described above, variation of any attribute of the OTC device 103 allows for adjustment of the compressive and reactive force constants thereof on the compressed tissue in the central region 107.

Figure 11:
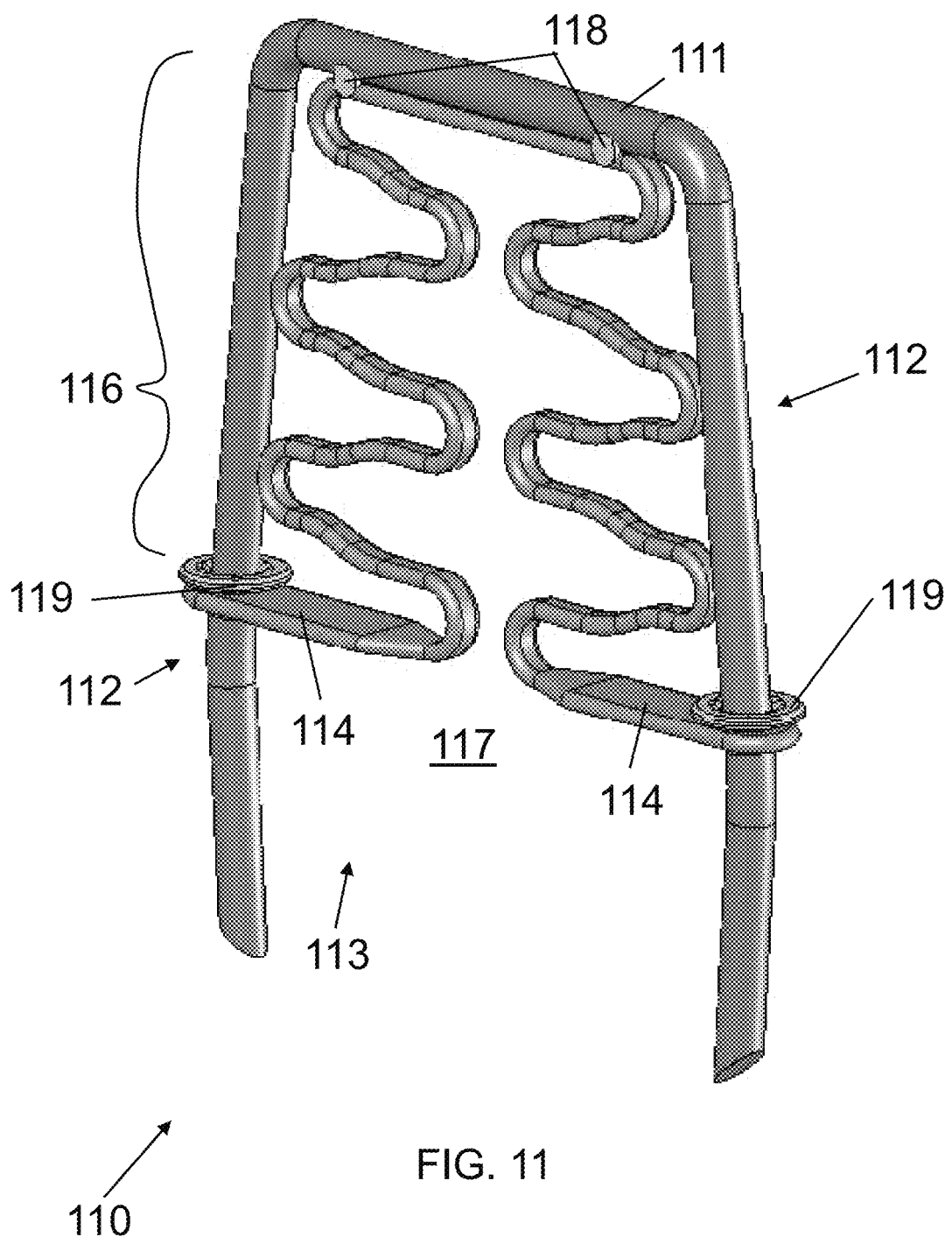
FIG. 11 is a perspective view from above a side of a tenth exemplary embodiment of an OTC staple according to the invention.
Figure 11A:
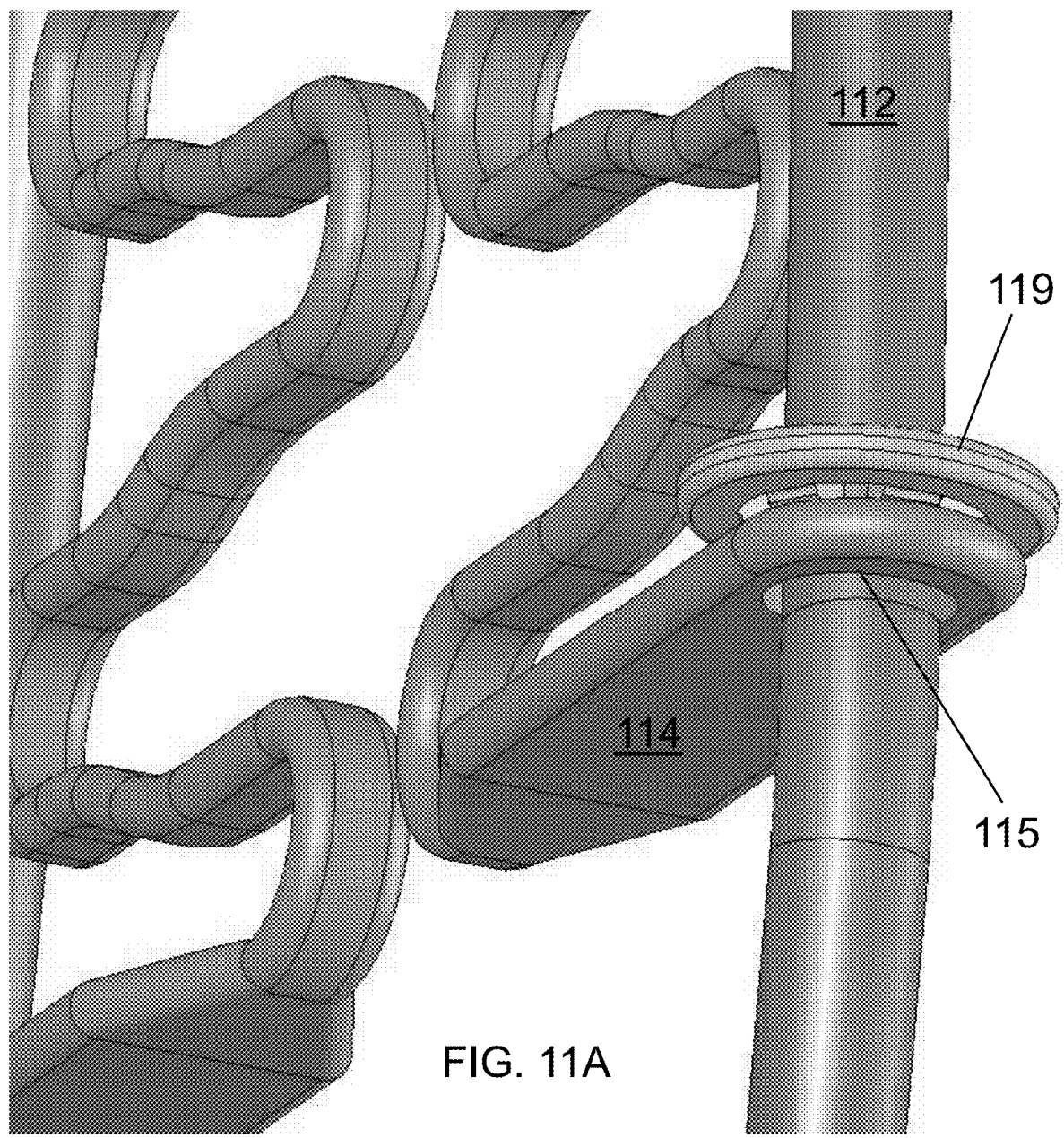
FIG. 11A is a fragmentary, enlarged perspective view from below a side of the OTC staple of FIG. 11.

FIGS. 11 and 11A illustrate a tenth exemplary embodiment of the OTC staple 110 according to the invention. This variation has some of the features of the above embodiments. In this variant, like the embodiment of FIG. 3, the OTC portion is symmetrical with respect to the bridge 111 and the legs 112, and the OTC device 113 is a separate part from the bridge 111 and legs 112 of the staple 110. The compressing portion 114 is like the embodiment of FIG. 10—it is formed from two compressing plates, each of these plates being attached to a respective lower end of two halves of the OTC device 113. The lowermost end of the extension 116 gradually increases in cross-section until it is equal in area to the compressing portion 114. Each compressing plate, then, extends towards a respective one of the legs 112 and defines a respective port 115 for receiving therein one of the legs 112. In FIG. 11, the ports 115 cannot be seen because of the presence of one-way washers 119 (described below), but the port 115 is visible in FIG. 11A.

As set forth above, each port 115 has a shape substantially corresponding to the cross-sectional shape of the upper portion of the legs 112 but is slightly larger. The legs 112 pass through each port 115 to form the OTC device 113. Because the ports 115 are shaped to be slightly larger than the cross-section of the legs 112, the extension 116 acts as a compression spring in the bridge-legs plane as the compressing portion 114 moves up and down along the upper portion of the legs 112. In this configuration, movement of the OTC device 113 out of the bridge-legs plane is substantially prevented. It is the extension 116 that provides the load-bearing force when tissue is compressed within the central region 117 of the staple 110. In this embodiment (like the embodiment of FIG. 10), the two sides of the OTC device 113 move independent from one another. Thus, if tissue varies in any characteristic within the central portion 117 (e.g., hardness, thickness, density), the optimal tissue compression force can be delivered independently and differently for each of the two differing tissue segments contacting the two plates of the compressing portion 114.

Introduced for the first time in this embodiment are one-way devices 119 (one exemplary embodiment being a star washer that is illustrated in FIGS. 11 and 11A) disposed on the leg 112 between the bridge 111 and the compressing portion 114. These devices 119 are shaped to freely move on the leg 112 upwards towards the bridge 111 but not to move in the opposite direction. Thus, as tissue is being compressed within the central region 117 as the distal ends of the legs 112 are curved in the stapling action, the tissue presses against the compressing portion 114 and moves the compressing portion 114 up towards the bridge 111. Once the stapling force is removed from the staple 110 (after stapling is complete), the tissue will most likely not press the washers 119 any further without any additionally supplied outside force. Thus, the washers 119 limit further movement of the compressing portion 114 from the then-current location of the washers 119 towards the first bend of the legs 112. These washers also add some friction when the first stapling movement occurs, which friction may be used to add to and make up the compression coefficients of the OTC device 113. If the stapled tissue swells, it is possible for the washers 119 to be moved if the force is sufficient. After such swelling ends and desiccation of the tissue occurs, the compressing portions 114 will be limited in further compression by these washers 119.

Like the previous embodiments, the OTC device 113 can be shaped with variations in cross-section and other spatial characteristics and can be formed with a variety of material compositions. Any portions of the extension 116 or the compressing portion 114 can be varied to have the same or varying cross-sectional areas (i.e., varying thicknesses). The extension 116 and the plates of the compressing portion 114 are, in this embodiment, different in cross-sectional areas. Here, the cross-sectional area of most of the extension 116 is smaller and narrower than the lowermost portion of the extension 116 and the cross-section of this lowermost portion gradually increases in width until it is equal to the cross-section of the respective plate of the compressing portion 114, which is substantially wider.

The extension 116 can be any shape or material so long as it delivers the pre-set compressive force to the tissue at the compressing portion 114 and as long as it allows for absorption of forces greater than this pre-set force. An exemplary embodiment selected for this OTC device 113 is a relatively sinusoidal curve traversing more than two sinusoidal periods and having a second "interior" curve. In this embodiment, the OTC device 113 has an uppermost portion that is (like the embodiments of FIGS. 8 to 10) a single bar extending along a majority of the bridge 111. Connection of the OTC device 113 to the staple 110, for example, at the bridge 111, can occur by any fastening measure. One exemplary connection method is spot welding, which is indicated in FIG. 11 by reference numeral 118. This process can be changed if desired. The type or types of material of the staple portions 111, 112 and the OTC device 113 will direct a preferable attachment method. In the case of attaching two materials together that are not suited to be welded, soldered or brazed, other attachment methods can be used such as crimping and adhesive bonding. Features can be added to one or both of the two components to facilitate the crimp or bond. These features could be configured to have the components snap together. In the case of dissimilar materials, for example, if the staple material is stainless steel and the OTC device 113 is of nickel titanium alloy, then preferred attachment measures include crimping, adhesive bonding, or snapping.

For illustrative purposes, the cross-section of the OTC device 113 has a racetrack shape, but can be changed as desired to other shapes (e.g., circular, ovular, polygonal, etc.). As described above, variation of any attribute of the OTC device 113 allows for adjustment of the compressive and reactive force constants thereof on the compressed tissue in the central region 117.

Figure 12:
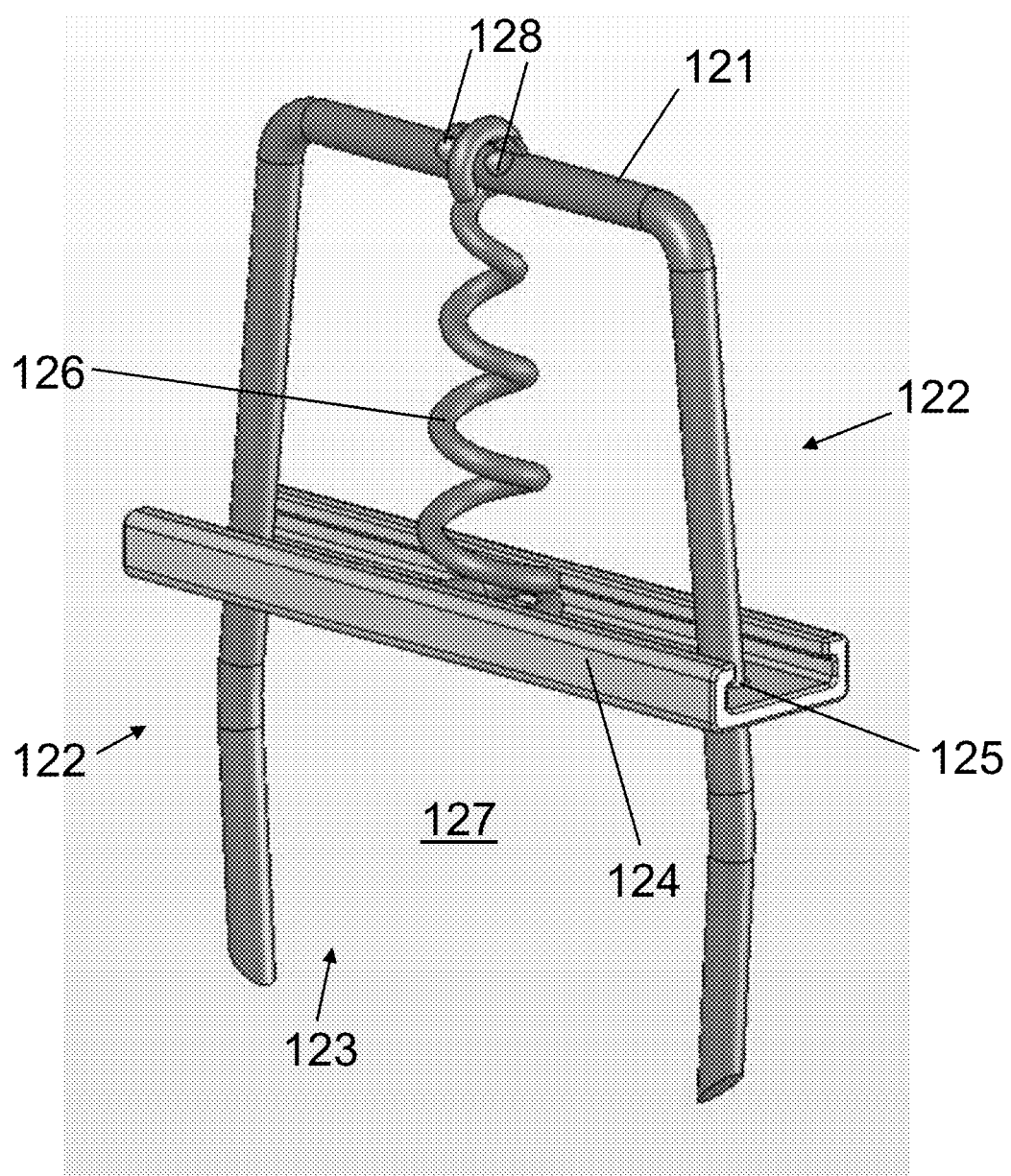
FIG. 12 is a perspective view from above a side of an eleventh exemplary embodiment of an OTC staple according to the invention.

FIG. 12 illustrates an eleventh exemplary embodiment of the OTC staple 120 according to the invention. This variation is significantly different from the above embodiments. The OTC device 123 is, as above, a separate part from the bridge 121 and legs 122 of the staple 120. Here, however, the compressing portion 124 is a C-beam having ports 125 that permit passage of a respective one of the legs 122 therethrough. Each port 125 has a shape substantially corresponding to the cross-sectional shape of the upper portion of the legs 122 but is slightly larger. The legs 122 pass through each port 125 to form the OTC device 123. In this configuration, movement of the OTC device 123 out of the bridge-legs plane is substantially prevented.

The C-beam shape is useful for a variety of reasons. First, the C-shape provides a central cavity in which a distal end of a compression device 126 can be held or fastened. Next, the C-shape also increases resistance to bending forces as compared to a simple rectangular plate, as is known in construction. Finally, orienting the open portion of the "C" away from the tissue presents a flat compressing plate to the tissue to be compressed. With such a shape, the tissue can be compressed evenly, with no singular pressure points. Of course, the C-shape is not the only possible cross-sectional shape. The compressing portion 124 can be a rectangular plate, an I-beam, an L-beam, or any other desired shape.

Figure 13:
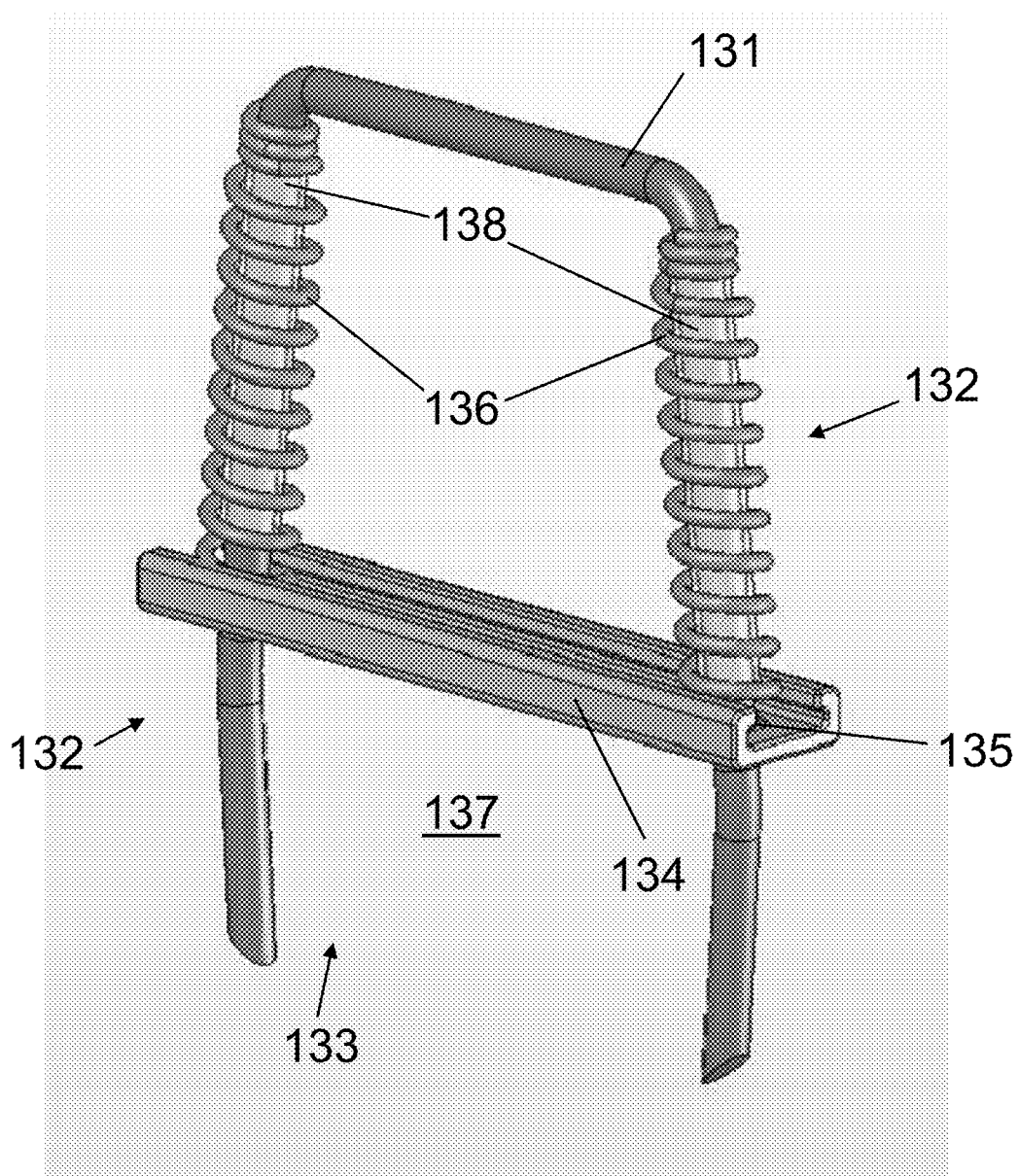
FIG. 13 is a perspective view from above a side of a twelfth exemplary embodiment of an OTC staple according to the invention.

The compression device 126 can take any form (see, e.g., FIG. 13). The exemplary embodiment of FIG. 12 illustrates the compression device 126 as a conically expanding compression spring. Connection of the spring 126 and compressing portion 124 to the staple 120, for example, at the bridge 121, can occur by any fastening measure. The illustrated exemplary proximal connection method is a ring of the spring material wrapping around the bridge 121. This proximal end is secured at the center of the bridge 121 and held in place there by placing protuberances 128 on the bridge 121. These protuberances prevent lateral movement of the proximal ring towards either of the two legs 122. Of course, this ring can be welded or fastened to the bridge 121 by any fastening process. The distal end of the spring is a relatively circular coil lying in the same plane as the interior cavity of the C-beam and having an outer diameter just slightly less than the interior diameter of the C-shaped cavity of the compressing portion 124. Thus, the ends of the C-shape can be used to retain the distal end of the spring 126 within the cavity. Of course, other fastening measures can be used to secure the spring distal ends to the compressing portion 124.

It is the spring 126 that provides the load-bearing force when tissue is compressed within the central region 127 of the staple 120. Like the previous embodiments, the OTC device 123 can be shaped with variations in cross-section, winding, and other spatial characteristics and can be formed with a variety of material compositions. Any portions of the spring 126 or the compressing portion 124 can be varied. In particular, the spring 126 can be any shape or material so long as it delivers the pre-set compressive force to the tissue through the compressing portion 124 and as long as it allows for absorption of forces greater than this pre-set force. As described above, variation of any attribute of the OTC device 123 allows for adjustment of the compressive and reactive force constants thereof on the compressed tissue in the central region 127.

FIG. 13 illustrates a twelfth exemplary embodiment of the OTC staple 130 according to the invention. This variation is similar to the embodiment of FIG. 12. The OTC device 133 is, as above, a separate part from the bridge 131 and legs 132 of the staple 130 and the compressing portion 134 is a C-beam having ports 135 that permit passage of a respective one of the legs 132 therethrough. Each port 135 has a shape substantially corresponding to the cross-sectional shape of the upper portion of the legs 132 but is slightly larger. The legs 132 pass through each port 135 to form the OTC device 133. In this configuration, movement of the OTC device 133 out of the bridge-legs plane is substantially prevented.

The C-beam shape has the same benefits as described in the eleventh embodiment of FIG. 12. Like that embodiment, the C-shape is not required; the compressing portion 134 can be a rectangular plate, an I-beam, an L-beam, or any other desired shape.

The compression device 136 can take any form. In the exemplary embodiment of FIG. 13, the compression device 136 is a pair of compression springs 136. Connection of these springs 136 and the compressing portion 134 to the staple 130, for example, at the bridge 131, can occur by any fastening measure. The illustrated exemplary proximal connection method is a narrowing of the spring diameter to be equal or less than the diameter of the legs 132 at the connection point to the bridge 131. Thus, the springs 136 can be held by the force imparted on the legs 132 by press-fitting the narrower spring rings onto a desired location on the legs 132. Alternatively and/or additionally, the almost ninety degree bend at the legs-bridge intersection forms a stop preventing further upward movement of the distal ends of each spring 136. Of course, the upper ring(s) can be fastened to the staple 130 by any measure, such as welding, crimping, etc.

Like the embodiment of FIG. 12, the distal end of the springs 136 in FIG. 13 is formed by a relatively circular coil lying in the same plane as the interior cavity of the C-beam and having an outer diameter just slightly less than the interior diameter of the C-shaped cavity of the compressing portion 134. Thus, the ends of the C-shape can be used to retain the distal end of the spring 136 within the cavity. The coils can be welded to the C-beam, for example. Of course, other fastening measures and coil configurations can be used to secure the distal ends of the springs 136 to the compressing portion 134.

It is the springs 136 that provide the load-bearing force when tissue is compressed within the central region 137 of the staple 130. Like the previous embodiments, the OTC device 133 can be shaped with variations in cross-section and other spatial characteristics and can be formed with a variety of material compositions. Any portions of the springs 136 or the compressing portion 134 can be varied. In particular, the spring 136 can be any shape or material so long as it delivers the pre-set compressive force to the tissue through the compressing portion 134 and as long as it allows for absorption of forces greater than this pre-set force. As described above, variation of any attribute of the OTC device 133 allows for adjustment of the compressive and reactive force constants thereof on the compressed tissue in the central region 137.

The spring 136 shown in FIG. 12 floats between the legs 132 and does not touch either leg 132. In contrast, the springs 135 of FIG. 13 wrap around the legs throughout the entire length. This orientation presents the possibility of resistance (i.e., friction) imparted upon the springs 136 by the legs 132 when the springs 136 are compressed. This resistance may be desirable depending upon the desired OTC device compression coefficient. If resistance is to be reduced, then sleeves 138 can be inserted onto the legs 132 such that they "lubricate" or reduce resistance of spring compression. These sleeves 138 can be made of polytetrafluoroethylene (PTFE), for example.

Figure 14:
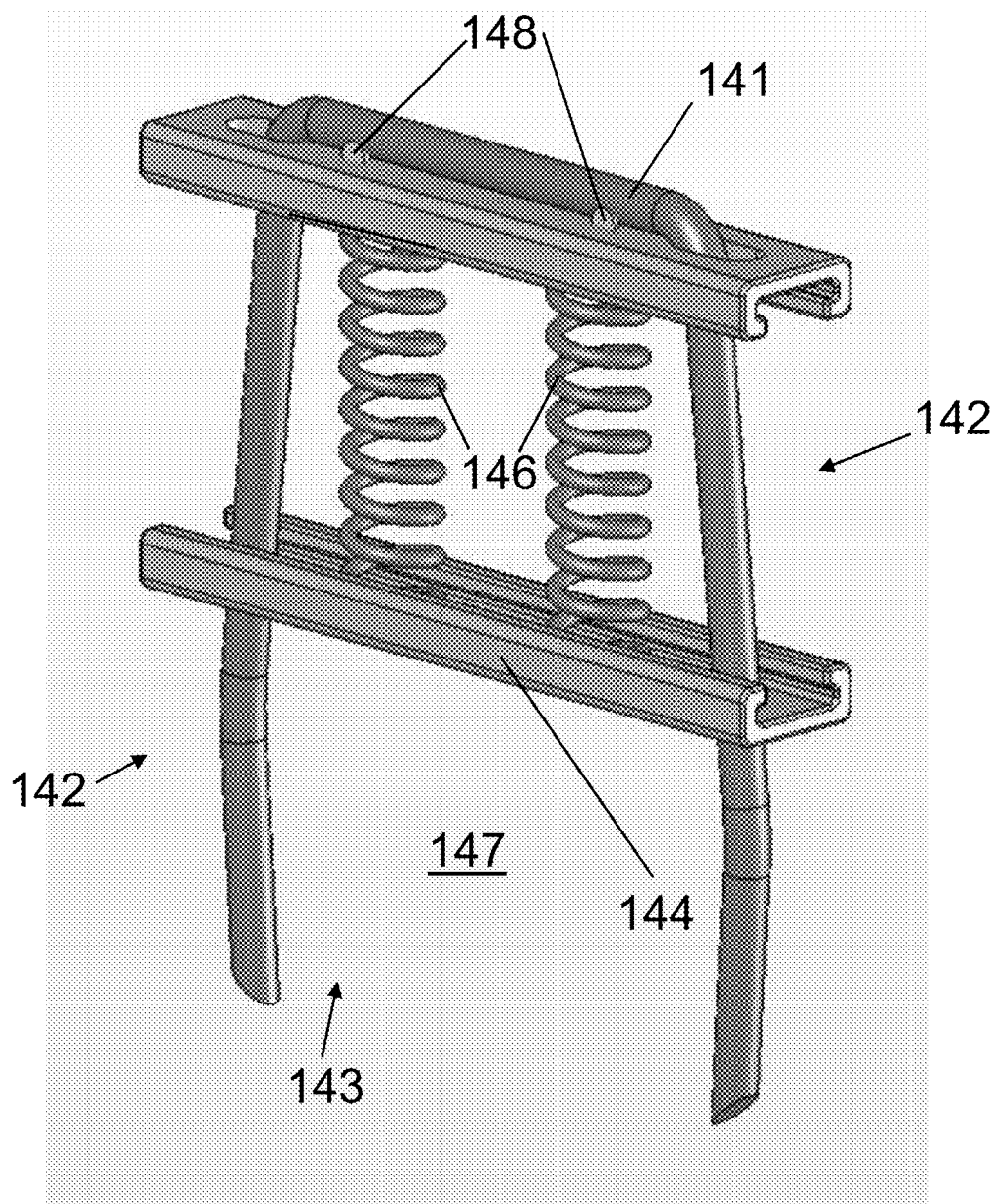
FIG. 14 is a perspective view from above a side of a thirteenth exemplary embodiment of an OTC staple according to the invention.

FIG. 14 illustrates a thirteenth exemplary embodiment of the OTC staple 140 according to the invention. This variation is similar to the embodiments of FIGS. 12 and 13. The OTC device 143 is, as above, a separate part from the bridge 141 and legs 142 of the staple 140 and the compressing portion 144 is a C-beam having non-illustrated ports that permit passage of a respective one of the legs 142 therethrough (in the view of FIG. 14, the ports are blocked from view by the C-beam). Each port has a shape substantially corresponding to the cross-sectional shape of the upper portion of the legs 142 but is slightly larger. The legs 142 pass through each port to form the OTC device 143. In this configuration, movement of the OTC device 143 out of the bridge-legs plane is substantially prevented.

The C-beam shape has the same benefits as described in the eleventh embodiment of FIG. 12. Like that embodiment, the C-shape is not required; the compressing portion 144 can be a rectangular plate, an I-beam, an L-beam, or any other desired shape.

The compression device 146 can take any form. The exemplary embodiment of FIG. 14 is a pair of compression springs 146. Like the single spring 136 shown in FIG. 12, the compression springs 146 of this embodiment float between the legs 142 and do not touch either leg 142. Connection of these springs 146 to the staple 140, for example, at the bridge 141, can occur by any fastening measure. The illustrated exemplary proximal connection method is a second C-beam disposed against the bridge 141 and connected thereto by any fastening measure, such as spot welds 148, for example. With such a connection configuration, each of the springs 146 can be formed with a relatively circular coil lying in the same plane as the interior cavity of each C-beam and having an outer diameter just slightly less than the interior diameter of the respective C-shaped cavity of the compressing portion 144. Thus, the ends of the C-shape can be used to retain the distal end of the spring 146 within the cavity. These end coils can be press-fit or slid into the C-beam cavity for connection thereto. Alternatively and/or additionally, these lower and upper loops can be fastened to the beams by welding, crimping, etc. The respective interior cavities of the two C-beams can be of different or of equal size.

It is the springs 146 that provide the load-bearing force when tissue is compressed within the central region 147 of the staple 140. Like the previous embodiments, the OTC device 143 can be shaped with variations in cross-section, winding, and other spatial characteristics and can be formed with a variety of material compositions. Any portions of the springs 146 or the compressing portion 144 can be varied. In particular, the spring 146 can be any shape or winding or of any material so long as it delivers the pre-set compressive force to the tissue through the compressing portion 144 and as long as it allows for absorption of forces greater than this pre-set force. As described above, variation of any attribute of the OTC device 143 allows for adjustment of the compressive and reactive force constants thereof on the compressed tissue in the central region 147.

Figure 15:
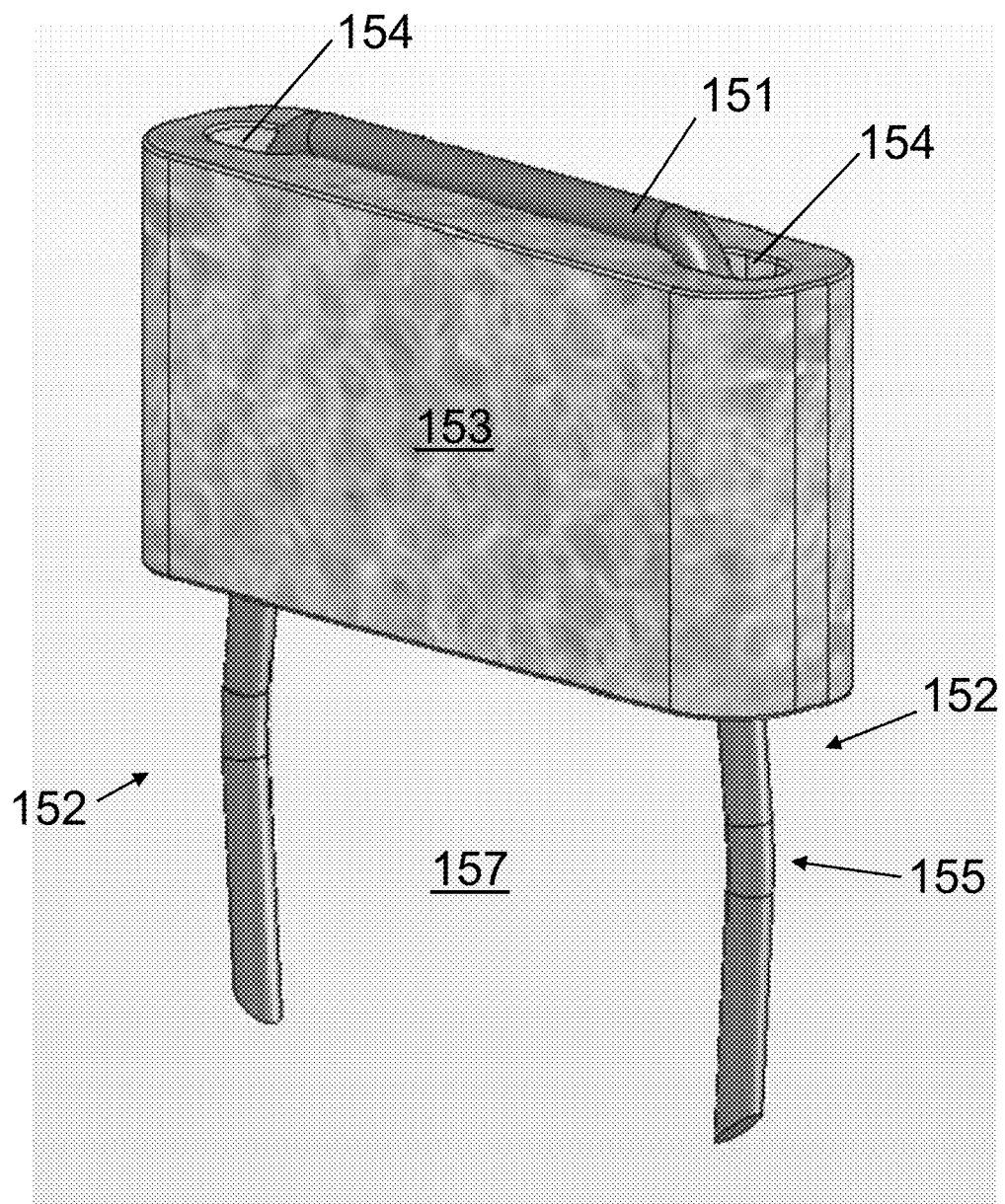
FIG. 15 is a perspective view from above a side of a fourteenth exemplary embodiment of an OTC staple according to the invention.

FIG. 15 illustrates a fourteenth exemplary embodiment of the OTC staple 150 according to the invention. The OTC device 153 is, as above, a separate part from the bridge 151 and legs 152 of the staple 150. Here, however, this variation differs from the previous embodiments because the OTC device 153 is a cushion made of a compressible material. Examples of such material include, but are not limited to, closed cell polyethylene foam, expanded polytetrafluoroethylene (PTFE), silicone rubber, silicone rubber foam, urethane, and electro-spun thermoplastic elastomers. This cushion 153 defines two channels 154 for receiving therethrough a respective one of the legs 152. Because the staple legs 152 taper inwards slightly in a direction from the intermediate portion 155 of the staple 150 to the ends of the bridge 151 (although this taper is not a requirement), the cross-sectional area of the channels 154 are larger than the cross-section of a portion of the legs 152 disposed inside the channels 154. By passing the legs 152 through each channel 154, the OTC device 153 is formed.

It is this pillow 153 that provides the load-bearing force when tissue is compressed within the central region 157 of the staple 150. Like the previous embodiments, the OTC device 153 can be shaped with variations in cross-section and other spatial characteristics and can be formed with a variety of material compositions. The exemplary embodiment illustrated in FIG. 15 is a pillow having a racetrack cross-sectional shape in the transverse direction. However, the pillow can be circular, ovular, rectangular, and polygonal in its outer transverse shape.

Any portion of the pillow 153 can be varied so long as it delivers the pre-set compressive force to the tissue at the distal end of the pillow 153 and as long as it allows for absorption of forces greater than this pre-set force. As described above, variation of any attribute of the OTC device 153 allows for adjustment of the compressive and reactive force constants thereof on the compressed tissue in the central region 157.

Figure 16:
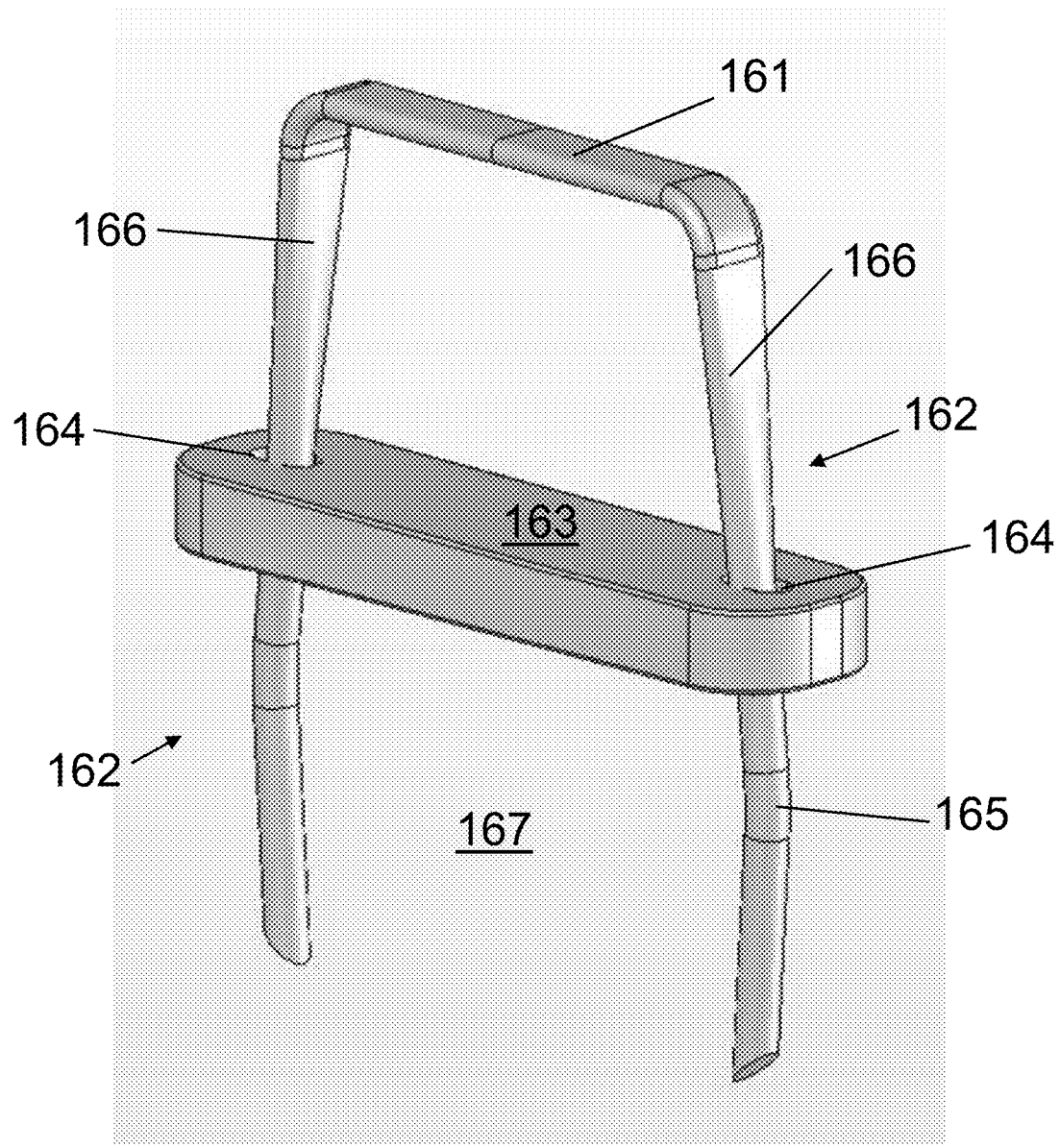
FIG. 16 is a perspective view from above a side of a fifteenth exemplary embodiment of an OTC staple according to the invention.
Figure 17:
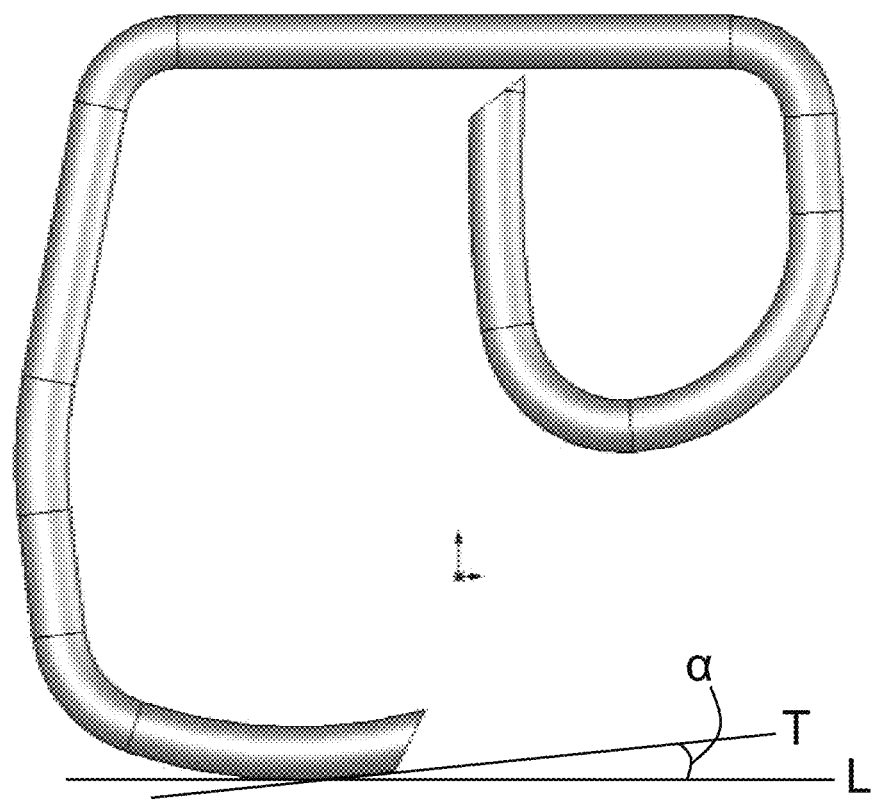
FIG. 17 is a side elevational view of the prior art surgical staple of FIG. 1 with the staple tips illustrating an exemplary range of stapling.
Figure 18:
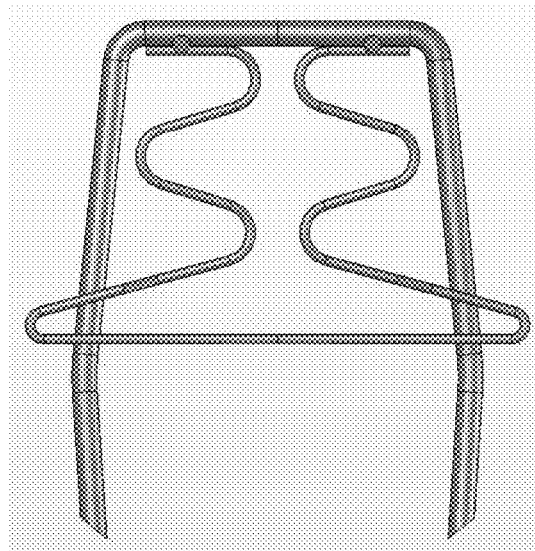
FIG. 18 is a side elevational view of the staple of FIG. 6 with the staple tips in a first intermediate position of an exemplary stapling range.
Figure 19:
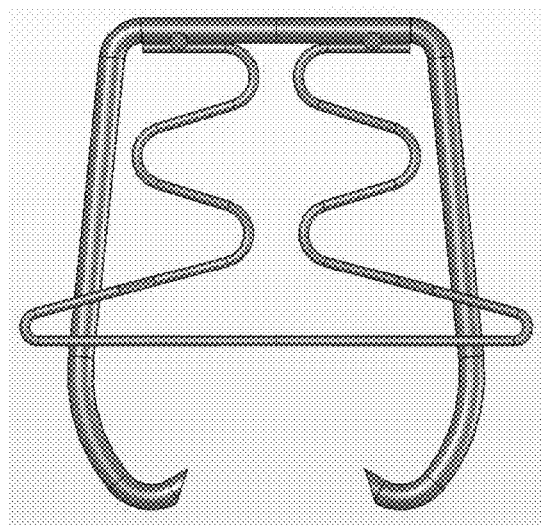
FIG. 19 is a side elevational view of the staple of FIG. 6 with the staple tips in a second intermediate position of an exemplary stapling range.
Figure 20:
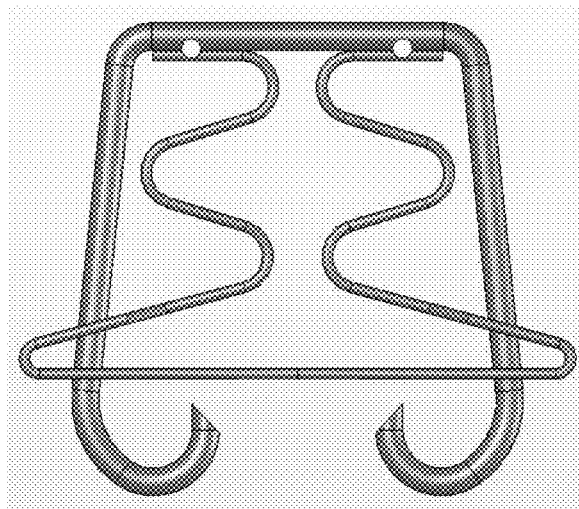
FIG. 20 is a side elevational view of the staple of FIG. 6 with the staple tips in a third intermediate position of an exemplary stapling range.

FIG. 16 illustrates a fifteenth exemplary embodiment of the OTC staple 160 according to the invention. This variation is different from the previous embodiments. The OTC device 163 is, as above, a separate part from the bridge 161 and legs 162 of the staple 160. The OTC device is a plate 163 made of a semi-compressible material having properties that will be described in detail below. Examples of such a material include, but are not limited to, polyurethane and silicone rubber. The plate 163 defines two channels 164 for receiving therethrough a respective one of the legs 162. Because the legs 162 taper inwards slightly in the bridge-legs plane in a direction from the intermediate portion 165 of the staple 160 to the ends of the bridge 161 (although this taper is not a requirement), the cross-sectional area of each of the channels 164 in the bridge-legs plane is larger than the cross-section of the legs 162 that are to be disposed inside the channels 164. This larger area is defined by a hole that is longer in the bridge-legs plane than in the plane orthogonal thereto along the axis of the leg 162. In the exemplary embodiment shown in FIG. 16, the cross-sectional shape of the channels 164 are ovular or racetrack shaped. By passing the legs 162 through each channel 164, the OTC device 163 is formed.

It is noted that the staple 160 shown in FIG. 16 is different from the prior art staple of FIG. 1. Specifically, the connecting portion 166 of the legs 162 tapers in width outwardly in the direction beginning from the intermediate portion towards the bridge 161 in a plane that is orthogonal to the bridge-legs plane. Because the channels 164 have a fixed width in the plane of the widening (which plane is orthogonal to the bridge-legs plane), and due to the fact that the fixed width is close in size to the lower-most portion of the connecting portion 166 (nearest to the intermediate portion 165), the plate 163 will not be able to move upwards towards the bridge 161 unless the material of the plate 163 is semi-compressible. Knowledge about the material's ability to compress and the resistance it provides to upward movement as the plate 163 progresses upward along the outwards taper of the leg widening can be used to set or adjust the compressive and reactive force constants thereof on the compressed tissue in the central region 167. Any portion of the plate 163 and of the upper leg taper can be varied so long as the OTC system (plate 163 and taper of the legs 162) delivers the pre-set compressive force to the tissue at the distal end of the plate 163 and as long as it allows for absorption of forces greater than this pre-set force.

The OTC device of this embodiment can be shaped with variations in cross-section, taper, and other spatial characteristics and can be formed with a variety of material compositions. The exemplary embodiment illustrated in FIG. 16 is a plate 163 having a racetrack cross-sectional shape in the transverse direction. However, the pillow can be circular, ovular, rectangular, and polygonal in its outer transverse shape, for example.

The OTC staple according to the invention is applied in the same manner as a conventional staple, that is:
the staple is loaded into a staple cartridge;
material to be stapled with the staple is placed between the staple cartridge and an anvil; and
the anvil and staple are brought together to press the lower portion of the legs against the anvil and bend the lower portions inward to capture the material in the central region and compress it between the bent portions and the compressing portion of the staple.

Because the material to be stapled has a length less than the distance between the bent lower portions and the bridge, the captured material partially compresses the OTC device inside the staple to, thereby, effect the optimal tissue compression feature. When the staple and material are released from the staple cartridge and anvil, the OTC device is imparting a pre-set compressive force against the compressed material. Significantly, the OTC device is able to move while the material is going through its compression and expansion cycle(s) until it finally reaches a steady state size. Even after reaching the steady state, the OTC device imparts the desired compressive force (within an acceptable minimum range) so that the material is not permanently damaged due to over-compression.

For example, if the material is human tissue, when tissue is stapled, liquid is forced out of the tissue. During the desiccation period, the tissue compresses further and further. The OTC device compensates by enlarging to follow the tissue compression. At some point in time, the tissue begins to swell (due to the puncturing and compressing forces imparted thereon). During the swelling period, the OTC device compensates by reducing to follow the tissue swelling.

The foregoing description and accompanying drawings illustrate the principles, preferred embodiments and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. A compression-self-adjusting staple, comprising:
a substantially U-shaped staple having:
a bridge;
two legs extending from the bridge at an angle thereto; and
a compression device:
at least partly disposed between the legs; and
having a bias portion with:
a compression surface movably disposed between the legs; and
a compression resistor:
connected to the bridge and to the compression surface; and
formed into a plurality of bends that resist movement of the compression surface towards the bridge with a pre-set compressive force.

2. The staple according to claim 1, wherein each of the legs have:
a base end integral with the bridge; and
a deformable distal end defining a stapling point shaped to pierce material to be stapled.

3. The staple according to claim 2, wherein the compression surface and the legs define a central compression region in which material is disposed and compressed between the compression surface and the stapling points when the distal ends of the legs are deformed.

4. The staple according to claim 3, wherein the compression resistor maintains the force during expansion and contraction of the material.

5. The staple according to claim 1, wherein:
due to the pre-set compressive force, stapling of tissue occurs within an optimal tissue compression range upon application of a stapling force; and
after stapling, the compression resistor maintains the pre-set compressive force within the optimal tissue compression range.

6. The staple according to claim 1, wherein the compression resistor is disposed between the bridge and the compression surface.

7. The staple according to claim 1, wherein the compression resistor is formed to resist movement of the compression surface towards the bridge with a constant force.

8. The staple according to claim 1, wherein the compression resistor is formed to resist movement of the compression surface towards the bridge with a linearly increasing force.

9. The staple according to claim 1, wherein the compression resistor has an anti-compressive spring constant imparting a constant anti-compressive force over an optimal tissue compression range.

10. The staple according to claim 1, wherein the compression resistor is sinusoidal.

11. The staple according to claim 1, wherein the compression surface is at a distance from the bridge.

12. The staple according to claim 1, wherein the compression surface is parallel to the bridge.

13. A method of stapling tissue during a surgical procedure, the method comprising:
piercing tissue with distal ends of leg portions of a surgical staple;
deforming at least the distal ends of the leg portions to compress a portion of the tissue between the distal ends and a compression surface of the surgical staple;
maintaining an optimal tissue compression force on the tissue with a compression resistor of the surgical staple, wherein the compression resistor is formed into a plurality of bends that resist movement of the compression surface in a proximal direction with a pre-set force.

14. The method according to claim 13, wherein the surgical staple is substantially U-shaped.

15. The method according to claim 13, wherein the leg portions are connected to a bridge portion of the surgical staple and the compression resistor is at least partly disposed between the compression surface and the bridge portion.

16. The method according to claim 15, wherein the compression surface is parallel to the bridge portion.

17. The method according to claim 13, wherein the pre-set force is within an optimal tissue compression force range.

18. The method according to claim 13, wherein the compression resistor maintains the force during expansion and contraction of the tissue.

19. The method according to claim 13, wherein the compression resistor is formed to resist movement of the compression surface in the proximal direction with a constant force.

20. The method according to claim 13, wherein the compression resistor is formed to resist movement of the compression surface in the proximal direction with a linearly increasing force.

* * * * *